US012583935B2

(12) United States Patent
Gu et al.

(10) Patent No.: US 12,583,935 B2
(45) Date of Patent: Mar. 24, 2026

(54) ANTI-HUMAN CD47 ANTIBODY AND ANTIGEN-BINDING FRAGMENT THEREOF, AND PREPARATION METHOD THEREFOR AND USE THEREOF

(71) Applicants: Suzhou Zelgen Biopharmaceuticals Co., Ltd., Suzhou (CN); Shanghai Zelgen Pharma.Tech Co., Ltd., Shanghai (CN)

(72) Inventors: Liyun Gu, Shanghai (CN); Yong Zhao, Shanghai (CN); Shifu Mo, Shanghai (CN); Wei Xu, Shanghai (CN); Jie Yang, Shanghai (CN); Dong Ding, Shanghai (CN); Zhichao Wang, Shanghai (CN)

(73) Assignees: Suzhou Zelgen Biopharmaceuticals Co., Ltd., Suzhou (CN); Shanghai Zelgen Pharma.Tech Co., Ltd., Shanghai (CN)

( * ) Notice: Subject to any disclaimer, the term of this patent is extended or adjusted under 35 U.S.C. 154(b) by 768 days.

(21) Appl. No.: 17/995,190

(22) PCT Filed: Mar. 31, 2021

(86) PCT No.: PCT/CN2021/084706
§ 371 (c)(1),
(2) Date: Sep. 30, 2022

(87) PCT Pub. No.: WO2021/197393
PCT Pub. Date: Oct. 7, 2021

(65) Prior Publication Data
US 2023/0167192 A1     Jun. 1, 2023

(30) Foreign Application Priority Data
Mar. 31, 2020    (CN) ......................... 202010240238.7

(51) Int. Cl.
*C07K 16/28* (2006.01)
*A61P 35/00* (2006.01)
*C12N 15/63* (2006.01)

(52) U.S. Cl.
CPC .......... *C07K 16/2896* (2013.01); *A61P 35/00* (2018.01); *C12N 15/63* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 11,267,885 B2 * | 3/2022 | Qiu .................... | C07K 16/2803 |
| 11,292,836 B2 | 4/2022 | Tsun et al. | |
| 2018/0142019 A1 | 5/2018 | Manning et al. | |
| 2022/0119517 A1 | 4/2022 | Wang et al. | |

FOREIGN PATENT DOCUMENTS

| | | | | |
|---|---|---|---|---|
| CN | 107955071 A | 4/2018 | | |
| CN | 110305214 A | 10/2019 | | |
| CN | 110862454 A | 3/2020 | | |
| WO | 2014123580 A | 8/2014 | | |
| WO | WO-2017186928 A1 * | 11/2017 | ......... | C07K 16/1282 |
| WO | 2018075857 A | 4/2018 | | |
| WO | 2018137705 A | 8/2018 | | |
| WO | 2018233575 A | 12/2018 | | |
| WO | 2019042119 A | 3/2019 | | |
| WO | 2019042285 A | 3/2019 | | |
| WO | 2019179366 A | 9/2019 | | |
| WO | WO-2019224711 A2 * | 11/2019 | .......... | C07K 16/468 |
| WO | 2020009725 A | 1/2020 | | |
| WO | WO-2020043044 A1 * | 3/2020 | ............. | C07K 16/28 |

OTHER PUBLICATIONS

ACS. Cancer Risk and Prevention. saved from website Mar. 21, 2025. (Year: 2025).*
Merriam-Webster. "Prevent" definition. saved from website Apr. 24, 2025. (Year: 2025).*
Russ et al. Blocking "don't eat me" signal of CD47-SIRPα in hematological malignancies, an in-depth review. Blood Reviews 32 (2018) 480-489. (Year: 2018).*
Sela-Culang et al. The structural basis of antibody-antigen recognition. Fron. Immuno., vol. 4, Article 302, Oct. 2013. (Year: 2013).*
Herold et al. Determinants of the assembly and function of antibody variable domains. Nature Scientific Reports, 7:12276, Sep. 25, 2017. (Year: 2017).*
International Search Report (Form PCT/ISA/210) for International Patent Application No. PCT/CN2021/084706, issued from the International Searching Authority, date of mailing Jul. 1, 2021, with English-language translation, 7 pages.
Written Opinion of the International Searching Authority (Form PCT/ISA/237) for International Patent Application No. PCT/CN2021/084706, issued from the International Searching Authority, date of mailing Jul. 1, 2021, with English-language translation, 6 pages.

* cited by examiner

*Primary Examiner* — Julie Wu
*Assistant Examiner* — Amy M. Chattin
(74) *Attorney, Agent, or Firm* — Ice Miller LLP

(57) ABSTRACT

Provided in the present invention are an anti-human CD47 antibody or an antigen-binding fragment thereof, and a preparation method therefor and the use thereof. Also provided in the present invention are an isolated polynucleotide encoding the antibody or the antigen-binding fragment thereof and a vector containing the isolated polynucleotide of the present invention. Further provided in the present invention is the use of the antibody or the antigen-binding fragment thereof according to the present invention in the preparation of a drug, the drug being used for treating and/or preventing a disease that benefits from an enhanced immune response, wherein the disease is cancer.

19 Claims, 7 Drawing Sheets

Specification includes a Sequence Listing.

SEQUENCE LISTING

```
<160> NUMBER OF SEQ ID NOS: 18

<210> SEQ ID NO 1
<211> LENGTH: 10
<212> TYPE: PRT
<213> ORGANISM: Artificial sequence
<220> FEATURE:
<223> OTHER INFORMATION: heavy chain complementarity determining region
      VH CDR1

<400> SEQUENCE: 1

Gly Phe Thr Phe Ser Asp Tyr Gly Met Ala
1               5                   10

<210> SEQ ID NO 2
<211> LENGTH: 17
<212> TYPE: PRT
<213> ORGANISM: Artificial sequence
<220> FEATURE:
<223> OTHER INFORMATION: heavy chain complementarity determining region
      VH CDR2

<400> SEQUENCE: 2

Phe Ile Thr Asn Leu Ala Ser Ser Ile Tyr Tyr Ala Asp Thr Val Thr
1               5                   10                  15

Gly

<210> SEQ ID NO 3
<211> LENGTH: 11
<212> TYPE: PRT
<213> ORGANISM: Artificial sequence
<220> FEATURE:
<223> OTHER INFORMATION: heavy chain complementarity determining region
      VH CDR3
```

<400> SEQUENCE: 3

Ala Arg Ala Gly Asp Tyr Arg Ser Phe Pro Tyr
1               5                   10

<210> SEQ ID NO 4
<211> LENGTH: 10
<212> TYPE: PRT
<213> ORGANISM: Artificial sequence
<220> FEATURE:
<223> OTHER INFORMATION: light chain complementarity determining region
      VL CDR1

<400> SEQUENCE: 4

Ser Ala Ser Ser Ser Val Asn Tyr Val Asn
1               5                   10

<210> SEQ ID NO 5
<211> LENGTH: 7
<212> TYPE: PRT
<213> ORGANISM: Artificial sequence
<220> FEATURE:
<223> OTHER INFORMATION: light chain complementarity determining region
      VL CDR2

<400> SEQUENCE: 5

Gly Ile Ser Asn Leu Ala Ser
1               5

<210> SEQ ID NO 6
<211> LENGTH: 8
<212> TYPE: PRT
<213> ORGANISM: Artificial sequence
<220> FEATURE:
<223> OTHER INFORMATION: light chain complementarity determining region
      VL CDR3

<400> SEQUENCE: 6

Gln Gln Arg Ser Thr Phe Pro Pro
1               5

<210> SEQ ID NO 7
<211> LENGTH: 118
<212> TYPE: PRT
<213> ORGANISM: Artificial sequence
<220> FEATURE:
<223> OTHER INFORMATION: Heavy chain variable region of the human-mouse
      chimeric antibody UM03-L4

<400> SEQUENCE: 7

Glu Val Lys Leu Val Glu Ser Gly Gly Asp Leu Val Gln Pro Gly Gly
1               5                   10                  15

Ser Arg Lys Leu Ser Cys Ala Ala Ser Gly Phe Thr Phe Ser Asp Tyr
            20                  25                  30

Gly Met Ala Trp Ile Arg Gln Ala Pro Gly Lys Gly Pro Glu Trp Ile
        35                  40                  45

Ala Phe Ile Thr Asn Leu Ala Ser Ser Ile Tyr Tyr Ala Asp Thr Val
    50                  55                  60

Thr Gly Arg Phe Thr Ile Ser Arg Glu Asn Ala Lys Asn Thr Leu Tyr
65                  70                  75                  80

Leu Glu Met Ser Ser Leu Arg Ser Glu Asp Thr Ala Met Tyr Tyr Cys
                85                  90                  95

Ala Arg Ala Gly Asp Tyr Arg Ser Phe Pro Tyr Trp Gly Gln Gly Thr
            100                 105                 110

```
Pro Val Thr Val Ser Ala
        115

<210> SEQ ID NO 8
<211> LENGTH: 107
<212> TYPE: PRT
<213> ORGANISM: Artificial sequence
<220> FEATURE:
<223> OTHER INFORMATION: Light chain variable region of the human-mouse
      chimeric antibody UM03-L4

<400> SEQUENCE: 8

Glu Ile Leu Leu Thr Gln Ser Pro Ala Ile Ile Ala Ala Ser Pro Gly
1               5                   10                  15

Glu Lys Val Thr Ile Thr Cys Ser Ala Ser Ser Ser Val Asn Tyr Val
            20                  25                  30

Asn Trp Tyr Gln Gln Lys Pro Gly Ser Ser Pro Lys Ile Trp Ile Tyr
        35                  40                  45

Gly Ile Ser Asn Leu Ala Ser Gly Val Pro Ala Arg Phe Ser Gly Ser
    50                  55                  60

Gly Ser Gly Thr Ser Phe Ser Phe Thr Ile Asn Ser Met Glu Ala Glu
65                  70                  75                  80

Asp Val Ala Thr Tyr Tyr Cys Gln Gln Arg Ser Thr Phe Pro Pro Tyr
                85                  90                  95

Thr Phe Gly Gly Gly Thr Lys Leu Glu Ile Lys
            100                 105

<210> SEQ ID NO 9
<211> LENGTH: 445
<212> TYPE: PRT
<213> ORGANISM: Artificial sequence
<220> FEATURE:
<223> OTHER INFORMATION: Heavy chain of human-mouse chimeric antibody
      UM03-L4

<400> SEQUENCE: 9

Glu Val Lys Leu Val Glu Ser Gly Gly Asp Leu Val Gln Pro Gly Gly
1               5                   10                  15

Ser Arg Lys Leu Ser Cys Ala Ala Ser Gly Phe Thr Phe Ser Asp Tyr
            20                  25                  30

Gly Met Ala Trp Ile Arg Gln Ala Pro Gly Lys Gly Pro Glu Trp Ile
        35                  40                  45

Ala Phe Ile Thr Asn Leu Ala Ser Ser Ile Tyr Tyr Ala Asp Thr Val
    50                  55                  60

Thr Gly Arg Phe Thr Ile Ser Arg Glu Asn Ala Lys Asn Thr Leu Tyr
65                  70                  75                  80

Leu Glu Met Ser Ser Leu Arg Ser Glu Asp Thr Ala Met Tyr Tyr Cys
                85                  90                  95

Ala Arg Ala Gly Asp Tyr Arg Ser Phe Pro Tyr Trp Gly Gln Gly Thr
            100                 105                 110

Pro Val Thr Val Ser Ala Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

-continued

```
Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
            210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 10
<211> LENGTH: 214
<212> TYPE: PRT
<213> ORGANISM: Artificial sequence
<220> FEATURE:
<223> OTHER INFORMATION: Light chain of human-mouse chimeric antibody
      UM03-L4

<400> SEQUENCE: 10

Glu Ile Leu Leu Thr Gln Ser Pro Ala Ile Ile Ala Ala Ser Pro Gly
1               5                   10                  15

Glu Lys Val Thr Ile Thr Cys Ser Ala Ser Ser Ser Val Asn Tyr Val
            20                  25                  30

Asn Trp Tyr Gln Gln Lys Pro Gly Ser Ser Pro Lys Ile Trp Ile Tyr
            35                  40                  45

Gly Ile Ser Asn Leu Ala Ser Gly Val Pro Ala Arg Phe Ser Gly Ser
            50                  55                  60

Gly Ser Gly Thr Ser Phe Ser Phe Thr Ile Asn Ser Met Glu Ala Glu
65                  70                  75                  80

Asp Val Ala Thr Tyr Tyr Cys Gln Gln Arg Ser Thr Phe Pro Pro Tyr
                85                  90                  95
```

-continued

```
Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 11
<211> LENGTH: 1335
<212> TYPE: DNA
<213> ORGANISM: Artificial sequence
<220> FEATURE:
<223> OTHER INFORMATION: The cDNA sequence encoding the UM03-L4 heavy
      chain

<400> SEQUENCE: 11
gaggtgaagc tggtggagag cggcggcgac ctggtgcagc caggaggatc cagaaagctg      60
agctgtgccg ccagcggctt cacattcagc gactacggca tggcctggat caggcaggcc     120
cctggcaagg gccccgagtg gatcgccttc atcaccaatc tggcctcctc catctactac     180
gccgacacag tgaccggcag gttcaccatc agcagagaga cgccaagaa cacactgtac      240 ctggagatgt cctccctgag aagcgaggac acagccatgt actactgtgc cagagccggc     300
gactacagga gcttccccta ctggggccag ggcacacctg tgaccgtgtc cgccgctagc     360
acaaagggcc ccagcgtgtt cctctggcc ccctgcagca gaagcaccag cgagtccacc      420
gccgccctgg gatgcctggt gaaggactac ttccctgagc ccgtgacagt gagctggaat     480
agcggcgccc tgacaagcgg cgtgcacacc tttcctgccg tgctgcagtc cagcggcctg     540
tacagcctga gcagcgtggt gacagtgcct agctcctccc tgggcacaaa gacatacacc     600
tgcaatgtgg accacaagcc cagcaacaca aaggtggaca gagagtgga gagcaagtac      660 ggccctcctt gtccccctg tcctgcccct gagtttctgg gcggcccctc cgtgtttctg      720
tttcctccca gcctaagga taccctgatg atctccagaa cccccgaggt gacctgtgtg      780
gtggtggatg tgagccagga ggaccccgag gtgcagttca ctggtacgt ggacggcgtg      840 gaggtgcaca tgccaagac caagcccagg gaggagcagt ttaactccac atacagggtg     900
gtgtccgtgc tgaccgtgct gcaccaggac tggctgaatg gcaaggagta caagtgtaag      960
gtgagcaaca agggcctgcc tagctccatc gagaagacca tctccaaggc caagggccag    1020
cctagggagc cccaggtgta cacactgcct cccagccagg aggagatgac aaagaaccag    1080
gtgagcctga catgcctggt gaaaggcttc taccctcag acatcgccgt ggagtgggag     1140
tccaacggcc agcctgagaa caattacaag acaacccccc ccgtgctgga ttccgacggc    1200
agctttttcc tgtactccag actgaccgtg gacaagagca gatggcagga gggcaatgtg    1260
tttagctgtt ccgtgatgca cgaggccctg cacaatcact acacacagaa gtccctgagc    1320
```

-continued

```
ctgagcctgg gcaaa                                                   1335

<210> SEQ ID NO 12
<211> LENGTH: 642
<212> TYPE: DNA
<213> ORGANISM: Artificial sequence
<220> FEATURE:
<223> OTHER INFORMATION: The cDNA sequence encoding the light chain
      UM03-L4

<400> SEQUENCE: 12
gagatcctgc tgacccagag ccccgccatc atcgccgcca gccctggaga gaaggtgacc        60
atcacatgtt ccgccagcag cagcgtgaat tacgtgaact ggtatcaaca gaagcctggc       120
agcagcccta agatctggat ctacggcatc tccaacctgg cctccggcgt gcctgccagg       180
ttcagcggaa gcggcagcgg caccagcttc agcttcacaa tcaatagcat ggaggccgag       240
gatgtggcca catactactg tcagcagaga tccacattcc ctccctacac attcggcggc       300
ggcaccaagc tggagatcaa gcgtacggtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag caccctgacg       540
ctgagcaaag cagactacga gaaacacaaa gtctacgcct gcgaagtcac ccatcagggc       600
ctgagttcgc ccgtcacaaa gagcttcaac aggggagagt gt                          642

<210> SEQ ID NO 13
<211> LENGTH: 118
<212> TYPE: PRT
<213> ORGANISM: Artificial sequence
<220> FEATURE:
<223> OTHER INFORMATION: Heavy chain variable region of humanized
      antibody UM03-C4

<400> SEQUENCE: 13

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Asp Tyr
            20                  25                  30

Gly Met Ala Trp Ile Arg Gln Ala Pro Gly Lys Gly Pro Glu Trp Ile
        35                  40                  45

Ala Phe Ile Thr Asn Leu Ala Ser Ser Ile Tyr Tyr Ala Asp Thr Val
    50                  55                  60

Thr Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Asp Tyr Arg Ser Phe Pro Tyr Trp Gly Gln Gly Thr
            100                 105                 110

Leu Val Thr Val Ser Ala
        115

<210> SEQ ID NO 14
<211> LENGTH: 107
<212> TYPE: PRT
<213> ORGANISM: Artificial sequence
<220> FEATURE:
<223> OTHER INFORMATION: Light chain variable region of humanized
      antibody UM03-C4
```

-continued

<400> SEQUENCE: 14

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Asn Tyr Val
                20                  25                  30

Asn Trp Tyr Gln Gln Lys Pro Gly Gln Ala Pro Arg Ile Leu Ile Tyr
            35                  40                  45

Gly Ile Ser Asn Leu Ala Ser Gly Val Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Thr Phe Pro Pro Tyr
                85                  90                  95

Thr Phe Gly Gln Gly Thr Lys Leu Glu Ile Lys
                100                 105
```

<210> SEQ ID NO 15
<211> LENGTH: 445
<212> TYPE: PRT
<213> ORGANISM: Artificial sequence
<220> FEATURE:
<223> OTHER INFORMATION: Heavy chain of humanized antibody UM03-C4

<400> SEQUENCE: 15

```
Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Asp Tyr
                20                  25                  30

Gly Met Ala Trp Ile Arg Gln Ala Pro Gly Lys Gly Pro Glu Trp Ile
            35                  40                  45

Ala Phe Ile Thr Asn Leu Ala Ser Ser Ile Tyr Tyr Ala Asp Thr Val
        50                  55                  60

Thr Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Asp Tyr Arg Ser Phe Pro Tyr Trp Gly Gln Gly Thr
                100                 105                 110

Leu Val Thr Val Ser Ala Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
        210                 215                 220

Pro Pro Cys Pro Ala Pro Glu Phe Leu Gly Gly Pro Ser Val Phe Leu
225                 230                 235                 240
```

```
Phe Pro Pro Lys Pro Lys Asp Thr Leu Met Ile Ser Arg Thr Pro Glu
            245             250             255

Val Thr Cys Val Val Val Asp Val Ser Gln Glu Asp Pro Glu Val Gln
            260             265             270

Phe Asn Trp Tyr Val Asp Gly Val Glu Val His Asn Ala Lys Thr Lys
            275             280             285

Pro Arg Glu Glu Gln Phe Asn Ser Thr Tyr Arg Val Val Ser Val Leu
    290             295             300

Thr Val Leu His Gln Asp Trp Leu Asn Gly Lys Glu Tyr Lys Cys Lys
305             310             315             320

Val Ser Asn Lys Gly Leu Pro Ser Ser Ile Glu Lys Thr Ile Ser Lys
            325             330             335

Ala Lys Gly Gln Pro Arg Glu Pro Gln Val Tyr Thr Leu Pro Pro Ser
            340             345             350

Gln Glu Glu Met Thr Lys Asn Gln Val Ser Leu Thr Cys Leu Val Lys
            355             360             365

Gly Phe Tyr Pro Ser Asp Ile Ala Val Glu Trp Glu Ser Asn Gly Gln
    370             375             380

Pro Glu Asn Asn Tyr Lys Thr Thr Pro Pro Val Leu Asp Ser Asp Gly
385             390             395             400

Ser Phe Phe Leu Tyr Ser Arg Leu Thr Val Asp Lys Ser Arg Trp Gln
            405             410             415

Glu Gly Asn Val Phe Ser Cys Ser Val Met His Glu Ala Leu His Asn
            420             425             430

His Tyr Thr Gln Lys Ser Leu Ser Leu Ser Leu Gly Lys
            435             440             445

<210> SEQ ID NO 16
<211> LENGTH: 214
<212> TYPE: PRT
<213> ORGANISM: Artificial sequence
<220> FEATURE:
<223> OTHER INFORMATION: Light chain of humanized antibody UM03-C4

<400> SEQUENCE: 16

Glu Ile Val Leu Thr Gln Ser Pro Ala Thr Leu Ser Leu Ser Pro Gly
1               5               10              15

Glu Arg Ala Thr Leu Ser Cys Ser Ala Ser Ser Ser Val Asn Tyr Val
            20              25              30

Asn Trp Tyr Gln Gln Lys Pro Gly Gln Ala Pro Arg Ile Leu Ile Tyr
            35              40              45

Gly Ile Ser Asn Leu Ala Ser Gly Val Pro Ala Arg Phe Ser Gly Ser
    50              55              60

Gly Ser Gly Thr Asp Phe Thr Leu Thr Ile Ser Ser Leu Glu Pro Glu
65              70              75              80

Asp Phe Ala Val Tyr Tyr Cys Gln Gln Arg Ser Thr Phe Pro Pro Tyr
            85              90              95

Thr Phe Gly Gln Gly Thr Lys Leu Glu Ile Lys Arg Thr Val Ala Ala
            100             105             110

Pro Ser Val Phe Ile Phe Pro Pro Ser Asp Glu Gln Leu Lys Ser Gly
            115             120             125

Thr Ala Ser Val Val Cys Leu Leu Asn Asn Phe Tyr Pro Arg Glu Ala
            130             135             140

Lys Val Gln Trp Lys Val Asp Asn Ala Leu Gln Ser Gly Asn Ser Gln
145             150             155             160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 17
<211> LENGTH: 1335
<212> TYPE: DNA
<213> ORGANISM: Artificial sequence
<220> FEATURE:
<223> OTHER INFORMATION: The cDNA sequence encoding the UM03-C4 heavy
      chain

<400> SEQUENCE: 17
caggtccagc tggtcgagtc aggcggcggc gtcgtgcagc ctggaggatc actgagactg      60
agctgcgcag ccagcggctt cacattcagc gactacggca tggcctggat cagacaggca     120
cccggcaaag ggccagagtg gattgctttc atcaccaacc tggccagcag catctactac     180
gccgacaccg tgacaggcag attcaccatc agcagagaca acagcaagaa cacactgtac     240
ctgcagatga acagcctgcg cgccgaggac accgccgtgt actactgcgc cagggccgga     300
gactacagat cctttcccta ctgggggcag ggaaccctgg tgaccgtcag cgccgctagc     360
accaagggcc catcggtctt ccccctggcg ccctgctcca ggagcacctc cgagagcaca     420
gccgccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct tgggcacgaa gacctacacc     600
tgcaacgtag atcacaagcc cagcaacacc aaggtggaca gagagttga gtccaaatat     660 ggtcccccat gcccaccatg cccagcacct gagttcctgg gggaccatc agtcttcctg     720 ttccccccaa aacccaagga cactctcatg atctcccgga cccctgaggt cacgtgcgtg     780
gtggtggacg tgagccagga gaccccgag gtccagttca actggtacgt ggatggcgtg     840
gaggtgcata atgccaagac aaagccgcgg gaggagcagt tcaacagcac gtaccgtgtg     900
gtcagcgtcc tcaccgtcct gcaccaggac tggctgaacg gcaaggagta caagtgcaag     960
gtctccaaca aaggcctccc gtcctccatc gagaaaacca tctccaaagc caaagggcag    1020 cccgagagc acaggtgta caccctgccc ccatcccagg aggagatgac caagaaccag    1080
gtcagcctga cctgcctggt caaaggcttc taccccagcg acatcgccgt ggagtgggag    1140
agcaatgggc agccggagaa caactacaag accacgcctc ccgtgctgga ctccgacggc    1200
tccttcttcc tctacagcag gctaaccgtg gacaagagca ggtggcagga ggggaatgtc    1260
ttctcatgct ccgtgatgca tgaggctctg cacaaccact acacacagaa gagcctctcc    1320
ctgtctctgg gtaaa                                                     1335
```

```
<210> SEQ ID NO 18
<211> LENGTH: 642
<212> TYPE: DNA
<213> ORGANISM: Artificial sequence
<220> FEATURE:
<223> OTHER INFORMATION: The cDNA sequence encoding the light chain
      UM03-C4

<400> SEQUENCE: 18
```

-continued

```
gagattgtgc tgacccagag ccccgccaca ctgagtctga gtcccggcga gagagcaaca        60
ctgagttgta gcgccagcag tagtgtgaac tacgtgaact ggtatcagca gaagcctgga       120
caggctccca gaatcctgat ctacggcatc tccaacctgg ccagcggagt gcccgccaga       180
ttcagcggaa gtggcagcgg gacagacttc accctgacca tcagcagcct ggaacccgag       240
gatttcgccg tgtactactg ccagcagaga agcaccttcc ccccctatac atttggccag       300
ggaaccaagc tggaaatcaa acgtacggtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag caccctgacg       540
ctgagcaaag cagactacga gaaacacaaa gtctacgcct gcgaagtcac ccatcagggc       600
ctgagttcgc ccgtcacaaa gagcttcaac aggggagagt gt                         642
```

ANTI-HUMAN CD47 ANTIBODY AND ANTIGEN-BINDING FRAGMENT THEREOF, AND PREPARATION METHOD THEREFOR AND USE THEREOF

CROSS-REFERENCE TO RELATED APPLICATIONS

This application is a Section 371 of International Application No. PCT/CN2021/084706, filed Mar. 31, 2021, which was published in the Chinese language on Oct. 7, 2021, under International Publication No. WO 2021/197393A1, which claims priority to Chinese Application No. 202010240238.7, filed Mar. 31, 2020, the disclosures of all of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "065946_36US1" and a creation date of Oct. 19, 2022, and having a size of 23.5 kb. The sequence listing submitted via EFS-Web is part of the specification and is herein incorporated by reference in its entirety.

TECHNICAL FIELD

The present invention relates to the technical field of biological immunity, and particularly to an anti-human CD47 antibody and an antigen-binding fragment thereof that can specifically bind to human CD47 protein and thus block the binding to SIRPα so as to block the inhibitory effect of tumor cells expressing CD47 on macrophages expressing SIRPα. The present invention further relates to a method for preparing the antibody or the antigen-binding fragment thereof, and use thereof.

BACKGROUND

CD47 is a transmembrane glycoprotein of 45-50 kD and is a member of the immunoglobulin (Ig) superfamily. It was found that the binding of highly expressed CD47 on tumor cells to ligand SIRPα on macrophages causes tyrosine phosphorylation of SIRPα and thus provides an inhibitory regulation signal to inhibit phagocytosis of the macrophages. Correspondingly, blocking the pathway can relieve the inhibitory effect on the phagocytosis of macrophages to tumor cells and improve the immune response of organisms to the tumor cells, thus providing a new way for the immunotherapy of tumors.

In antitumor therapies targeting the CD47-SIRPα axis, the predominant mechanism is the activation of macrophages that enhances the phagocytosis of tumor cells by macrophages. Second, blocking CD47 may further recruit macrophages in tumor tissues, and recruit additional immune cell cytokines and chemokines, such as monocyte chemoattractant protein 3 (MCP-3), to tumor tissue, and the secretion of the cytokines contributes to the efficacy of CD47 blocking therapy. Again, therapies targeting CD47-SIRPα may also alter the polarization state of macrophages in tumors. Macrophages can be classified into M1 (type I) and M2 (type II) according to phenotype and functional activity. M1 macrophages can produce a large amount of pro-inflammatory cytokines, mediate resistance to intracellular parasites and inhibit tumor growth; M2 macrophages produce fewer pro-inflammatory molecules, and participate in tissue damage repair, angiogenesis and promotion of tumor growth. It was also reported that blocking CD47-SIRPα significantly increased M1 macrophage edema in the mouse tumor microenvironment, whereas mouse M2 macrophages did not show significant increase. Finally, other immune cells may also respond to CD47 blocking therapies. SIRPα is highly expressed on bone marrow immune cells, and thus it may be a key regulator of the bone marrow lineages. In mice, CD47 regulates antigen uptake by SIRPα⁺ dendritic cells, and the therapeutic effect of CD47 blockade was found to be dependent on dendritic cells using a homologous immunocompetent tumor model. Therapies targeting the CD47-SIRPα axis can promote adaptive immune responses in tumors by stimulating antigen presentation of macrophages or dendritic cells.

CD47 is widely expressed on a variety of cells, and particularly highly expressed on new erythrocytes. Thus the therapeutic antibodies targeting CD47 may likely cause anemia. On the other hand, the concentration of free anti-human CD47 antibody in vivo is also greatly reduced due to the binding of anti-human CD47 antibody to erythrocytes.

Therefore, stronger binding capacity to CD47 protein on tumor cell surface and weaker binding capacity to CD47 protein on erythrocyte surface have become targets of developing novel therapeutic anti-human CD47 antibodies.

SUMMARY

The present invention is mainly intended to provide an anti-human CD47 antibody of high potency and safety. The present invention further provides a method for preparing the antibody and use thereof. The anti-human CD47 antibody disclosed herein has strong binding capacity to CD47 protein on tumor cell surface and weak binding capacity to CD47 protein on erythrocyte surface, and thus can be used for treating various cancers by regulating immunologic function in human.

In one aspect, the present invention provides an anti-human CD47 antibody or an antigen-binding fragment thereof comprising one or more heavy chain complementarity determining regions selected from:

a VH CDR1 comprising an amino acid sequence set forth in SEQ ID NO: 1;

a VH CDR2 comprising an amino acid sequence set forth in SEQ ID NO: 2; and a VH CDR3 comprising an amino acid sequence set forth in SEQ ID NO: 3.

According to the present invention, the anti-human CD47 antibody or the antigen-binding fragment thereof further comprises one or more light chain complementarity determining regions selected from:

a VL CDR1 comprising an amino acid sequence set forth in SEQ ID NO: 4;

a VL CDR2 comprising an amino acid sequence set forth in SEQ ID NO: 5; and a VL CDR3 comprising an amino acid sequence set forth in SEQ ID NO: 6.

According to the present invention, the anti-human CD47 antibody or the antigen-binding fragment thereof is a camelized single domain antibody, an scFv, an scFv dimer, a BsFv, a dsFv, a dsFv2, a dsFv-dsFv', an Fv fragment, an Fab, an Fab', an F(ab')2, a ds bifunctional antibody, a nanobody, a domain antibody or a bivalent domain antibody;

preferably, the anti-human CD47 antibody or the antigen-binding fragment thereof further comprises a human heavy chain constant region and/or a human light chain constant region; more preferably, the human heavy chain constant region is selected from a heavy chain constant region of human IgG1, IgG2, IgG3 and IgG4, and the human light chain constant region is selected from a light chain constant region of human IgG1, IgG2, IgG3 and IgG4; even more preferably, the human heavy chain constant region is a heavy chain constant region of human IgG1 and the human light chain constant region is a κ chain.

In one embodiment according to the present invention, the anti-human CD47 antibody or the antigen-binding fragment thereof has a heavy chain variable region comprising an amino acid sequence set forth in SEQ ID NO: 7.

In one embodiment according to the present invention, the anti-human CD47 antibody or the antigen-binding fragment thereof has a light chain variable region comprising an amino acid sequence set forth in SEQ ID NO: 8.

In one embodiment according to the present invention, the anti-human CD47 antibody or the antigen-binding fragment thereof has a heavy chain comprising an amino acid sequence set forth in SEQ ID NO: 9.

In one embodiment according to the present invention, the anti-human CD47 antibody or the antigen-binding fragment thereof has a light chain comprising an amino acid sequence set forth in SEQ ID NO: 10.

In one embodiment according to the present invention, the anti-human CD47 antibody or the antigen-binding fragment thereof has a heavy chain variable region comprising an amino acid sequence set forth in SEQ ID NO: 13.

In one embodiment according to the present invention, the anti-human CD47 antibody or the antigen-binding fragment thereof has a light chain variable region comprising an amino acid sequence set forth in SEQ ID NO: 14.

In one embodiment according to the present invention, the anti-human CD47 antibody or the antigen-binding fragment thereof has a heavy chain comprising an amino acid sequence set forth in SEQ ID NO: 15.

In one embodiment according to the present invention, the anti-human CD47 antibody or the antigen-binding fragment thereof has a light chain comprising an amino acid sequence set forth in SEQ ID NO: 16.

In another aspect, the present invention further provides an isolated polynucleotide encoding the antibody or the antigen-binding fragment thereof described above.

Preferably, the polynucleotide comprises a nucleotide sequence set forth in SEQ ID NO: 11.

Preferably, the polynucleotide comprises a nucleotide sequence set forth in SEQ ID NO: 12.

Preferably, the polynucleotide comprises a nucleotide sequence set forth in SEQ ID NO: 17.

Preferably, the polynucleotide comprises a nucleotide sequence set forth in SEQ ID NO: 18.

In still another aspect, the present invention further provides a vector comprising the isolated polynucleotide disclosed herein.

In still yet another aspect, the present invention further provides a host cell comprising the vector disclosed herein. Preferably the host cell is a mammalian cell, more preferably a human, murine, ovine, equine, canine or feline cell, and even more preferably a Chinese hamster ovary cell.

Furthermore, the present invention further provides a method for preparing the antibody or the antigen-binding fragment thereof disclosed herein, comprising culturing the host cell in a condition for expressing the polynucleotide disclosed herein.

Furthermore, the present invention further provides a kit comprising the antibody or the antigen-binding fragment thereof disclosed herein.

Furthermore, the present invention further provides a pharmaceutical composition comprising the antibody or the antigen-binding fragment thereof disclosed herein and a pharmaceutically acceptable carrier.

Furthermore, the present invention further provides use of the antibody, or the antigen-binding fragment thereof disclosed herein in preparing a medicament or a cell for cell therapy for preventing and/or treating a disorder that would benefit from enhancing the immune response.

In one embodiment according to the present invention, the disorder is a cancer. Preferably the disorder is a lymphoma highly expressing CD47, such as acute myeloid leukemia and myelodysplastic syndrome.

Compared with the prior art, the anti-human CD47 antibody disclosed herein has strong binding capacity to CD47 protein on tumor cell surface, weak binding capacity to CD47 protein on erythrocyte surface and no agglutination effect on erythrocytes, and is a prospective novel therapeutic anti-human CD47 antibody.

BRIEF DESCRIPTION OF THE DRAWINGS

Embodiments of the present invention are described in detail below with reference to the accompanying drawings.

FIG. 2 illustrates the binding of the anti-human CD47 antibody disclosed herein to human/mouse tumor cells highly expressing human/murine CD47.

FIG. 4A illustrates the binding of the anti-human CD47 antibodies UM03-L4 and UM03-C4 disclosed herein and the positive control antibody to human erythrocytes; FIG. 4B illustrates that the anti-human CD47 antibodies UM03-L4 and UM03-C4 disclosed herein had little agglutination effect on human erythrocytes, and the positive control antibody had strong agglutination effect on human erythrocytes.

FIG. 5 illustrates the binding of the anti-human CD47 chimeric antibody disclosed herein to monkey erythrocytes and the agglutination effect on monkey erythrocytes.

DETAILED DESCRIPTION

Figure 1:
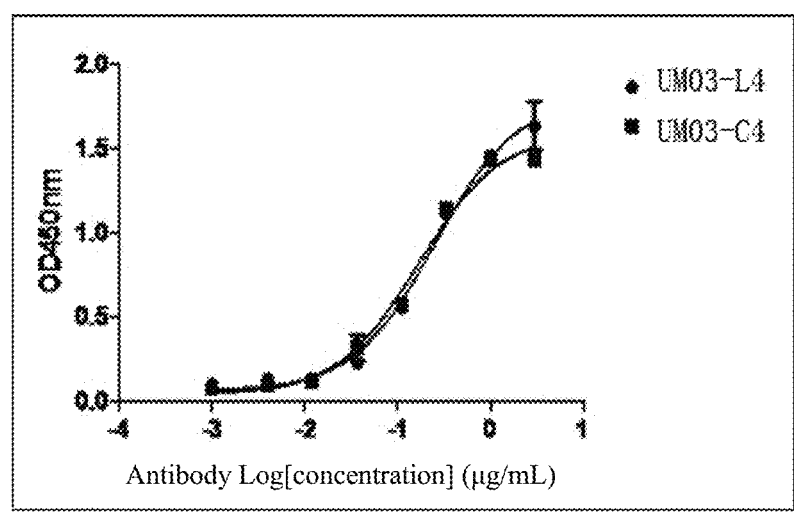
FIG. 1 is a graph illustrating the binding assay of the anti-human CD47 antibody disclosed herein to CD47 protein by ELISA.

The following description of the present application is intended to be illustrative of various embodiments of the present application. Therefore, specific modifications discussed herein should not be construed as limiting the scope of the present application. Numerous equivalents, changes and modifications can readily be devised by those skilled in the art without departing from the scope of the present application, and it should be understood that such equivalents are included within the scope of the present invention. All references, including publications, patents, and patent applications, cited in the present application are incorporated by reference in their entireties.

Definitions

The term "antibody" used herein includes any immunoglobulin, monoclonal antibody, polyclonal antibody, multispecific antibody or bispecific (bivalent) antibody that binds to a particular antigen. A natural intact antibody comprises two heavy chains and two light chains. Each heavy chain consists of one variable region and first, second and third constant regions; each light chain consists of one variable region and one constant region. Mammalian heavy chains can be classified into α, δ, ε, γ and μ, and mammalian light chains into λ and κ. Antibodies are "Y" shaped, with the neck of the Y configuration consisting of the second and third constant regions of the two heavy chains, which are bound by disulfide bonds. Each arm of the Y configuration includes the variable region and the first constant region of one of the heavy chains combined with the variable region and constant region of one of the light chains. The variable regions of the light and heavy chains determine the binding to antigens. The variable region of each chain comprises three hypervariable regions, called complementarity determining regions (CDRs). The CDRs of the light chain (L) are LCDR1, LCDR2 and LCDR3, and the CDRs of the heavy chain (H) are HCDR1, HCDR2 and HCDR3. The CDR boundaries of the antibody or the antigen-binding fragment thereof disclosed herein may be designated or identified by the Kabat, Chothia or Al-Lazikani numbering scheme. (Al-Lazikani, B., Chothia, C., Lesk, A. M., *J. Mol. Biol.*, 273(4):927 (1997); Chothia, C. et al., *J. Mol. Biol.*, 186(3): 651-63 (1985); Chothia, C. and Lesk, A. M., *J. Mol. Biol.*, 196:901 (1987); Chothia, C. et al., *Nature*, 342(6252):877-83 (1989); Kabat, E. A. et al., National Institutes of Health, Bethesda, Md. (1991)). The three CDRs are separated by continuous flanking portions called framework regions (FRs) that are more conserved than the CDRs and form a scaffold-supporting hypervariable loop. The constant regions of the heavy and light chains are not associated with antigen binding, but have various effector functions. Antibodies can be classified into several types depending on the amino acid sequence of the heavy chain constant region. Depending on the α, δ, ε, γ or μ heavy chain, antibodies can be classified into five major types or isotypes: IgA, IgD, IgE, IgG and IgM. Several major antibody types can also be classified into subtypes, such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain), among others.

The term "antigen-binding fragment" used herein refers to an antibody portion comprising one or more CDRs or any other antibody fragment that binds to an antigen but does not have an intact antibody structure. Examples of antigen-binding fragments include, but are not limited to, antibodies such as bifunctional antibody, Fab, Fab', F(ab')2, Fv fragment, disulfide stabilized Fv fragment (dsFv), (dsFv)2, bispecific dsFv (dsFv-dsFv'), disulfide stabilized bifunctional antibody (ds bifunctional antibody), single-chain variable fragment (scFv), scFv dimer (bivalent bifunctional antibody), bivalent single-chain variable fragment (BsFv), multispecific antibody, camelized single domain antibody, nanobody, domain antibody and bivalent domain antibody. The antigen-binding fragment may bind to the same antigen as the parent antibody. In certain embodiments, an antigen-binding fragment may comprise one or more CDRs from a particular human antibody grafted to framework regions from one or more different human antibodies.

The term "Fab" fragment of an antibody refers to a portion of an antibody molecule consisting of one light chain (comprising the variable and constant regions) and the variable region and a part of the constant regions of one heavy chain, which are bound by disulfide bonds. The term "Fab'" fragment refers to an Fab fragment comprising a part of the hinge region.

The term "F(ab')2" refers to a dimer of Fab.

Fc fragment of an antibody is responsible for a variety of different effector functions such as ADCC and CDC, but is not involved in antigen binding.

The term "Fv" fragment of an antibody refers to the smallest antibody fragment that comprises the entire antigen-binding sites. The Fv fragment consists of the variable region of one light chain and the variable region of one heavy chain.

The term "single-chain Fv antibody" or "scFv" refers to an engineered antibody consisting of a light chain variable region and a heavy chain variable region ligated directly or via a peptide chain (Huston J S et al, *Proc. Natl. Acad. Sci. USA*, 85:5879 (1988)).

The term "single-chain variable fragment Fv-Fc" or "scFv-Fc" refers to an engineered antibody consisting of an scFv ligated to the Fc fragment of an antibody.

The term "camelized single domain antibody", "heavy chain antibody" or "HCAb (Heavy-chain-only antibodies, HCAb)" refers to an antibody that comprises two VH domains and no light chain (Riechmann L. and Muyldermans S., *J. Immunol. Methods*, 231(1-2):25-38 (1999); Muyldermans S., *J. Biotechnol.*, 74(4):277-302 (2001); WO94/04678; WO94/25591; U.S. Pat. No. 6,005,079). The heavy chain antibody was originally derived from Camelidae species (camels, dromedaries and llamas). Despite the absence of light chains, camelized antibodies have confirmed complete antigen binding functions (Hamers Casterman C. et al., *Nature*, 363(6428):446-8 (1993); Nguyen V K. et al., "Heavy-chain antibodies in Camelidae: a case of evolutionary innovation", *Immunogenetics*, 54(1):39-47 (2002); Nguyen V K. et al., *Immunology*, 109(1):93-101 (2003)). The variable region (VH domain) of the heavy chain antibody is the smallest known antigen-binding unit produced by acquired immunity (Koch-Nolte F. et al., *FASEB J.*, 21(13):3490-8. Epub (2007)).

The term "nanobody" refers to an antibody fragment consisting of one VH domain from a heavy chain antibody and two constant regions CH2 and CH3.

The term "bifunctional antibody" comprises a small antibody fragment with two antigen-binding sites, wherein the fragment comprises a VH domain and a VL domain ligated on one polypeptide chain (see Holliger P. et al., *Proc. Natl. Acad. Sci. USA*, 90(14): 6444-8 (1993); EP404097; WO93/11161). The linker between the two domains is short that the two domains on the same chain cannot pair with each other, thereby forcing the two domains to pair with the complementary domains of the other chain, forming two antibody binding sites. The two antibody binding sites may specifically bind to the same or different antigens (or epitopes).

The term "domain antibody" refers to an antibody fragment comprising only one heavy chain variable region or one light chain variable region. In some cases, two or more VH domains are covalently bound by one polypeptide linker to form a bivalent domain antibody. The two VH domains of the bivalent domain antibody may target to the same or different antigens.

In certain embodiments, "(dsFv)2" comprises three peptide chains: two VH genes are ligated via a polypeptide linker and are ligated to two VL groups by disulfide bonds.

In certain embodiments, a "bispecific ds bifunctional antibody" comprises VL1-VH2 (ligated via a polypeptide linker) and VH1-VL2 (also ligated via a polypeptide linker) which are bound by disulfide bonds between VH1 and VL1.

The term "bispecific dsFv" or "dsFv-dsFv" comprises three polypeptide chains: a VH1-VH2 group, a VL1 group and a VL2 group, wherein the heavy chains are ligated via a polypeptide linker (e.g., a long flexible linker) and are bound by disulfide bonds to VL1 and VL2 groups, respectively, and each pair of heavy and light chains paired by disulfide bonds have different antigen specificity.

In certain embodiments, an "scFv dimer" is a bivalent bifunctional antibody or bivalent single-chain variable fragment (BsFv) comprising two dimerized VH-VL (ligated via a polypeptide linker) groups, wherein the VH of each group cooperate with the VL of the other group, respectively, to form two binding sites that can specifically bind to the same antigen (or epitope) or to different antigens (or epitopes). In some other embodiments, an "scFv dimer" is a bispecific bifunctional antibody comprising $V_{L1}$-$V_{H2}$ (ligated via a polypeptide linker) and $V_{H1}$-$V_{L2}$ (ligated via a polypeptide linker) bound to each other, wherein $V_{H1}$ and $V_{L1}$ cooperate, $V_{H2}$ and $V_{L2}$ cooperate, and the cooperating pairs have different antigen specificities.

The term "fully human" used herein, when used in reference to an antibody or antigen-binding fragment, refers to that the antibody or the antigen-binding fragment comprises or consists of an amino acid sequence that corresponds to an amino acid sequence of an antibody produced by human or human immune cells or derived from a non-human source, e.g., a transgenic non-human animal that utilizes a human antibody library, or other sequence encoding a human antibody. In certain embodiments, the fully human antibody does not comprise amino acid residues (particularly antigen-binding residues) derived from a non-human antibody.

The term "humanized" used herein, when applied to an antibody or an antigen-binding fragment, refers to that the antibody or the antigen-binding fragment comprises CDRs derived from a non-human animal, FR regions derived from human, and constant regions derived from human (where applicable). Since humanized antibodies or antigen-binding fragments have reduced immunogenicity, they are useful in certain embodiments as therapeutics for human. In some embodiments, the non-human animal is a mammal such as mouse, rat, rabbit, goat, sheep, guinea pig or hamster. In some embodiments, the humanized antibody or antigen-binding fragment consists essentially of sequences of human source, except for the non-human CDR sequences. In some embodiments, the FR region derived from human may comprise the same amino acid sequence as the human antibody from which it is derived, or it may comprise some amino acid alterations, for example, no more than 10, 9, 8, 7, 6, 5, 4, 3, 2, or 1 amino acid alteration. In some embodiments, the amino acid alteration may be present only in the heavy chain FR regions, only in the light chain FR regions, or in both chains. In some preferred embodiments, the humanized antibody comprises human FRI-3 and human JH and JK.

The term "chimeric" used herein refers to an antibody or an antigen-binding fragment comprising a portion of a heavy and/or light chain derived from one species, and the remainder of the heavy and/or light chain derived from a different species. In an illustrative example, a chimeric antibody may comprise constant regions derived from human and variable regions derived from a non-human animal, such as a mouse.

The term "CD47" refers to a ligand that binds to SIRPα. It is also referred to as TAP, MER6, OA3, etc. It has a molecular weight of 35.2 kDa and is stored in SwissProt in Accession No. Q08722.

The term "specifically binding" or "specific binding" used herein refers to a non-random binding reaction between two molecules, such as a reaction between an antibody and an antigen. In certain embodiments, the antibody or the antigen-binding fragment thereof disclosed herein specifically binds to human and/or monkey CD47 with a binding affinity $(K_D) \leq 10^{-6}$ M. $K_D$ used herein refers to the ratio of dissociation rate to association rate $(k_{off}/k_{on})$, which can be determined by surface plasmon resonance, for example using instruments such as Biacore.

The term "UM03-L4" used herein refers to a human-mouse chimeric antibody having a heavy chain set forth in SEQ ID NO: 9 and a light chain set forth in SEQ ID NO: 10, with the heavy and light chain constant regions being human IgG4 and κ chain, respectively.

The term "UM03-C4" used herein refers to a humanized antibody having a heavy chain set forth in SEQ ID NO: 15 and a light chain set forth in SEQ ID NO: 16, with the heavy and light chain constant regions being human IgG4 and κ chain, respectively.

The term "conservative substitution", when used in reference to an amino acid sequence, refers to that one amino acid residue is substituted with another amino acid residue having a side chain with similar physicochemical properties. For example, conservative substitutions may occur between hydrophobic side chain amino acid residues (e.g., Met, Ala, Val, Leu and Ile), between neutral hydrophilic side chain residues (e.g., Cys, Ser, Thr, Asn and Gln), between acidic side chain residues (e.g., Asp and Glu), between basic side chain amino acids (e.g., His, Lys and Arg), or between aromatic side chain residues (e.g., Trp, Tyr and Phe). It is known in the art that conservative substitutions do not generally result in significant changes in the conformational structure of a protein, and therefore can retain the biological activity of the protein.

The term "percent sequence identity", when used in reference to amino acid sequences (or nucleic acid sequences), refers to the percentage of amino acid (or nucleic acid) residues in a candidate sequence that are identical to those in a reference sequence in an alignment of the sequences where, if necessary, gaps can be introduced to maximize the number of identical amino acids (or nucleic acids). Conservative substitutions of the amino acid residues may or may not be considered as identical residues. Sequences can be aligned by means known in the art to determine the percent sequence identity of amino acid (or nucleic acid) sequences. Those skilled in the art can use default parameters for the means or adjust the parameters appropriately according to the needs of the alignment, e.g., by choosing a suitable algorithm.

The term "T cell" used herein includes $CD4^+$ T cells, $CD8^+$ T cells, T helper 1 cells, T helper 2 cells, T helper 17 cells and suppressor T cells.

The term "effector function" used herein refers to the biological activity of the Fc region of an antibody to bind to its effectors such as C1 complexes and Fc receptors. Exemplary effector functions include complement dependent cytotoxicity (CDC) induced by interaction of the antibody with C1q on the C1 complex, antibody dependent cell-mediated cytotoxicity (ADCC) induced by binding of the Fc region of the antibody to Fc receptors on effector cells, and phagocytosis.

The term "cancer" or "cancerous condition" used herein refers to any medical condition that is mediated by the growth, proliferation or metastasis of neoplastic or malignant cells and that causes solid and non-solid tumors, such as leukemia. The term "tumor" used herein refers to a solid substance of a tumor and/or malignant cells.

The term "treatment" or "therapy" of a condition includes preventing or alleviating the condition, reducing the rate of development or progression of a condition, reducing the risk of developing a condition, preventing or delaying development of symptoms associated with a condition, reducing or terminating symptoms associated with a condition, producing a complete or partial reversal of a condition, curing a condition, or a combination thereof. "Treatment" or "therapy" with respect to a cancer may refer to inhibiting or slowing the growth, reproduction, or metastasis of a tumor or malignant cells, or a combination thereof. "Treatment" or "therapy" with respect to a tumor includes eliminating all or a part of the tumor, inhibiting or slowing tumor growth and metastasis, preventing or delaying tumor progression, or a combination thereof.

"Isolated" substances have been artificially altered from its natural state. If an "isolated" substance or component occurs in nature, it has been altered or removed from its original state, or both. For example, a polynucleotide or polypeptide naturally present in a living animal is not isolated, but is considered as "isolated" if the polynucleotide or polypeptide is sufficiently separated from substances with which it coexists in its natural state, and is present in a sufficiently pure state. In certain embodiments, the antibody or the antigen-binding fragment has a purity of at least 90%, 93%, 95%, 96%, 97%, 98% or 99%, as determined by electrophoresis (e.g., SDS-PAGE, isoelectric focusing, capillary electrophoresis) or chromatography (e.g., ion exchange chromatography or reverse-phase HPLC).

The term "vector" used herein refers to a vehicle into which a polynucleotide encoding a protein is operatively inserted for expression of the protein. The vector may be used to transform, transduce or transfect a host cell such that the carried genetic material element is expressed in the host cell. For example, the vector includes: plasmids, phagemids, cosmids, artificial chromosomes such as yeast artificial chromosomes (YACs), bacterial artificial chromosomes (BACs) or P1-derived artificial chromosomes (PACs), bacteriophages such as lambda phages or M13 bacteriophages, animal viruses, and the like. Animal virus species used as vectors include retroviruses (including lentiviruses, adenoviruses, adeno-associated viruses, herpes viruses (e.g., herpes simplex virus), poxviruses, baculoviruses, papillomaviruses, and papovaviruses (e.g., SV40)). A vector may comprise a variety of elements that control expression, including promoter sequences, transcription initiation sequences, enhancer sequences, selection elements and reporter genes. In addition, the vector may further comprise a replication initiation site. The vector may further comprises components that facilitate the entry into cells, including, but not limited to, viral particles, liposomes, or protein capsids.

The term "host cell" used herein refers to a cell into which an exogenous polynucleotide and/or a vector is introduced.

The term "therapeutically effective amount" or "effective dose" used herein refers to a dose or concentration of a drug effective to treat a disease. For example, for use of the antibody or the antigen-binding fragment thereof disclosed herein, a therapeutically effective amount refers to the dose or concentration at which the antibody or the antigen-binding fragment thereof can eliminate all or a part of a tumor, inhibit or slow tumor growth, inhibit tumor cell metastasis, alleviate any symptoms or markers associated with a tumor or cancerous condition, prevent or delay the progression of a tumor or cancerous condition, inhibit or eliminate a virus or virus-infected cells, or a combination thereof.

The term "pharmaceutically acceptable" refers to that in general, a carrier, vehicle, diluent, adjuvant and/or salt is chemically and/or physically compatible with the other ingredients of the formulation and physiologically compatible with the recipient.

The term "cell therapy" refers to a method of treatment in which biologically active cellular material is transplanted into a patient to produce a desired therapeutic effect. In some specific embodiments, the cell therapy is achieved by engineering a particular cell such that the cell expresses an antibody or an antigen-binding fragment thereof, with the purpose of increasing the therapeutic effect of the cell or enhancing its ability to specifically work on a particular tissue site.

Anti-Human CD47 Antibody Disclosed Herein

In certain embodiments, the present application provides an exemplary anti-human CD47 antibody, UM03-C4.

It will be appreciated by those skilled in the art that the foregoing CDR sequences may be modified to comprise substitutions of one or more amino acids, thereby resulting in improved biological activity such as improved binding affinity for human CD47. For example, libraries of antibody variants (e.g., Fab or FcFv variants) can be produced and expressed using phage display technology, and screened for antibodies having affinity for human CD47. In another example, computer software can be used to simulate the binding of the antibody to human CD47 and to identify the amino acid residues on the antibody that form the binding interface. Such residues can be protected from substitutions to prevent a decrease in binding affinity, or can be the target of substitution to provide stronger binding. In certain embodiments, at least one (or all) substitutions in a CDR sequence are conservative substitutions.

In certain embodiments, the antibody or the antigen-binding fragment comprises one or more CDR sequences having at least 80% (e.g., at least 85%, 88%, 90%, 91%, 92%, 93%, 94%, 95%, 96%, 97%, 98% or 99%) sequence identity to SEQ ID NOs: 1-6, and retains a binding affinity for human CD47 similar to or even higher than that of the parent antibody. The parent antibody has substantially identical sequences, but the corresponding CDR sequences have 100% sequence identity to those set forth in SEQ ID NOs: 1-6.

In some embodiments, the antibody or the antigen-binding fragment disclosed herein is capable of specifically binding to human CD47 with a binding affinity $(K_D) \leq 10^{-7}$ M, as measured by surface plasmon resonance. The binding affinity value can be expressed as a $K_D$ value, which is calculated as the ratio of dissociation rate to association rate $(k_{off}/k_{on})$ when the binding of the antigen and the antigen-binding molecule reaches equilibrium. The antigen-binding affinity (e.g., $K_D$) may appropriately be determined by suitable methods known in the art, for example, including plasmon resonance binding using instruments such as Biacore.

In certain embodiments, the antibody or the antigen-binding fragment disclosed herein binds to human CD47 with an $EC_{50}$ (i.e., half maximal effective concentration) of 10 ng/mL to 10 µg/mL. Binding of the antibody or the antigen-binding fragment to human CD47 can be determined by methods known in the art, such as sandwich methods (e.g., ELISA), Western blot, FACS, or other binding assays. In an illustrative example, the test antibody (i.e., primary antibody) was bound to immobilized human CD47 or cells expressing human CD47. Unbound antibodies were washed away, and a labeled secondary antibody capable of binding to the primary antibody and thus detecting the bound secondary antibody was introduced. The detection was performed on a plate reader when CD47 was immobilized, or was performed using FACS analysis when cells expressing human CD47 were used.

The antibody is specific for human CD47. In certain embodiments, the antibody does not bind to murine CD47, but has similar binding affinities for monkey CD47 and human CD47.

In some embodiments, the antibody has a constant region of the IgG4 isotype with reduced or eliminated effector functions. Effector functions such as ADCC and CDC can result in cytotoxicity to cells expressing CD47. Some normal cells are capable of expressing CD47. To avoid potential undesirable toxicity to these normal cells, certain embodiments of the antibodies disclosed herein have reduced or even eliminated effector functions. Numerous assays are known for assessing ADCC or CDC activity, such as Fc receptor binding assay, complement C1q binding assay and cell lysis, which can be readily selected by those skilled in the art. Without wishing to be bound by theory, it is believed that antibodies with reduced or eliminated effector functions such as ADCC and CDC cause no or minimized cytotoxicity to cells expressing CD47 (e.g., those normal cells), thus avoiding undesirable adverse effects.

In some embodiments, the antibody or the antigen-binding fragment disclosed herein has reduced adverse effects. For example, the anti-human CD47 antibody and the antigen-binding fragment thereof can have fully human IgG sequences and are therefore less immunogenic than humanized antibodies. For another example, the antibody and the antigen-binding fragment thereof may have an IgG2 or IgG4 form to eliminate ADCC and CDC.

In some embodiments, the antibody disclosed herein is advantageous in that it can be used in combination with immunogenic substance, such as tumor cells, purified tumor antigens, cells transfected with encoding immunostimulatory factors and tumor vaccines. Furthermore, the anti-human CD47 antibody and the antigen-binding fragment thereof can be included in a combination therapy, including standard chemotherapy and radiation therapy, target-based small molecule therapy, and other emerging immune checkpoint modulator therapies. In some embodiments, the antibody and the antigen-binding fragment thereof can be used as the base molecule for antibody-drug conjugates, bispecific or multivalent antibodies.

In some embodiments, the antibody and the antigen-binding fragment thereof disclosed herein is camelized single domain antibody, bifunctional antibody, scFv, scFv dimer, BsFv, dsfv, (dsFv)2, dsFv-dsFv', Fv fragment, Fab, Fab', F(ab')2, ds bifunctional antibody, nanobody, domain antibody or bivalent domain antibody.

In some embodiments, the antibody disclosed herein comprises an immunoglobulin constant region. In some embodiments, the immunoglobulin constant region comprises a heavy chain and/or light chain constant region. The heavy chain constant region comprises the CH1, CH1-CH2 or CH1-CH3 regions. In some embodiments, the immunoglobulin constant region may further comprise one or more modifications to acquire a desired property. For example, the constant region may be modified to reduce or eliminate one or more effector functions to enhance FcRn receptor binding or to introduce one or more cysteine residues.

In certain embodiments, the antibody and the antigen-binding fragment thereof further comprise a conjugate. It is contemplated that the antibody or the antigen-binding fragment thereof disclosed herein may be ligated to a variety of conjugates (see, e.g., "Conjugate Vaccines", Contributions to Microbiology and Immunology, J. M. Cruse and R. E. Lewis, Jr. (Eds.), Carger Press, New York (1989)). These conjugates may be ligated to the antibody or the antigen-binding fragment thereof by covalent binding, affinity binding, insertion, coordinate binding, complexation, binding, mixing, addition, or the like. In certain embodiments, the antibodies and antigen-binding fragments disclosed herein can be engineered to comprise specific sites other than the epitope-binding portion that can be used to bind one or more conjugates. For example, such sites may comprise one or more reactive amino acid residues, such as cysteine residues and histidine residues, for facilitating covalent ligation to the conjugate. In certain embodiments, the antibody may be ligated indirectly to the conjugate, or via another conjugate. For example, the antibody or the antigen-binding fragment thereof can be ligated to a biotin, followed by indirect ligation to a second conjugate that is ligated to an avidin. The conjugate may be a detectable label, a pharmacokinetic modifying moiety, a purifying moiety, or a cytotoxic moiety. Examples of detectable labels may include fluorescent labels (e.g., fluorescein, rhodamine, dansyl, phycoerythrin or Texas Red), enzyme substrate labels (e.g., horseradish peroxidase, alkaline phosphatase, luciferase, glucoamylase, lysozyme, carbohydrate oxidase or β-D-galactosidase), stable or radioactive isotopes, chromophore moieties, digoxin, biotin/avidin, DNA molecules or gold for detection. In certain embodiments, the conjugate may be a pharmacokinetic modifying moiety such as PEG, which helps to extend the half-life of the antibody. Other suitable polymers include, for example, carboxymethyl cellulose, dextran, polyvinyl alcohol, polyvinyl pyrrolidone, ethylene glycol/propylene glycol copolymer, and the like. In certain embodiments, the conjugate can be a purifying moiety such as a magnetic bead. The "cytotoxic moiety" may be any agent that is harmful to cell or may damage or kill cells. Examples of cytotoxic moieties include, but are not limited to, paclitaxel, cytochalasin B, gramicidin D, ethidium bromide, emetine, mitomycin, etoposide, teniposide, vincristine, vinblastine, colchicine, doxorubicin, daunorubicin, dihydroxyanthrax dione, mitoxantrone, mithramycin, actinomycin D, 1-dehydrotestosterone, glucocorticoids, procaine, tetracaine, lidocaine, propranolol, puromycin and an analog thereof, antimetabolites (e.g., methotrexate, 6-mercaptopurine, 6-mercaptoguanine, cytarabine, 5-fluorouracil dacarbazide), alkylating agents (e.g., nitrogen mustard, thiotepa, chlorambucil, melphalan, carmustine (BSNU) and lomustine (CCNU), cyclophosphamide, busulfan, dibromomannitol, streptozotocin, mitomycin C, and cis-dichlorodiamine platinum (DDP), and cisplatin), anthracyclines (e.g., daunorubicin (formerly daunomycin) and doxorubicin), antibiotics (e.g., dactinomycin (formerly actinomycin), bleomycin, mithramycin and amikacin (AMC)), and antimitotics (e.g., vincristine and vinblastine).

Polynucleotides and Recombination Methods

The amino acid sequence of the antibody and the antigen-binding fragment thereof disclosed herein can be converted into a corresponding DNA coding sequence using genetic engineering techniques well known in the art. Due to the codon degeneracy, the DNA sequences resulting from the transformation may be completely identical, while the encoded protein sequence remains unchanged.

A vector comprising the polynucleotide encoding the antibody and the antigen-binding fragment thereof can be introduced into a host cell for cloning (amplification of DNA) or gene expression using recombinant techniques well known in the art. In another embodiment, the antibody and the antigen-binding fragment thereof can be acquired by homologous recombination methods well known in the art. Various vectors are available for selection. The vector component generally includes, but is not limited to, two or more of the following: a signal sequence, a replication initiation site, one or more marker genes, an enhancer sequence, a promoter (e.g., SV40, CMV and EF-1a) and a transcription termination sequence.

In some embodiments, the vector system includes a mammalian, bacterial or yeast system, etc., and will include plasmids for example, but not limited to, pALTER, pBAD, pcDNA, pCal, pL, pELpGEMEX, pGEX, pCLpCMV, pEGFP, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS420, pLexA, pACT2, and other vectors available from laboratories or the market. Suitable vectors may include plasmids or viral vectors (e.g., replication-defective retroviruses, adenoviruses and adeno-associated viruses).

The vector comprising the polynucleotide encoding the antibody and the antigen-binding fragment thereof may be introduced into a host cell for cloning or gene expression. Host cells suitable for cloning or expressing the DNA in the vector disclosed herein are prokaryotic cells, yeasts or the above-mentioned higher eukaryotic cells. Prokaryotic cells suitable for use in the present invention include eubacteria such as gram-negative or gram-positive bacteria, for example, Enterobacteriaceae, e.g., *Escherichia coli, Enterobacter, Erwinia, Klebsiella, Proteus, Salmonella*, e.g., *S. typhimurium, Serratia*, e.g., *S. marcescens, Shigella*, Bacilli, e.g., *B. subtilis* and *B. licheniformis, Pseudomonas*, e.g., *P. aeruginosa*, and Streptomycetaceae.

In addition to prokaryotic cells, eukaryotic microorganisms such as filamentous fungi or yeasts may also be used as host cells for cloning or expression of vectors encoding the antibody or the antigen-binding fragment thereof. *Saccharomyces cerevisiae* is the most commonly used lower eukaryotic host microorganism. However, many other commonly used genera, species and strains are suitable for use in the present invention, for example: *Schizosaccharomyces pombe; Kluyveromyces* hosts such as *K. lactis, K. fragilis* (ATCC12424), *K. bulgaricus* (ATCC16045), *K. wickeramii* (ATCC24178), *K. waltii* (ATCC56500), *K. drosophilarum* (ATCC36906), *K. thermotolerans* and *K. marxianus: Yarrowia lipolytica* (EP402226); *Pichia pastoris* (EP183,070); *Candida; Trichoderma reesei* (EP244234); *Neurospora*

*crassa; Schwanniomyces occidentalis*, such as *Schwanniomyces occidentalis*; and filamentous fungi, e.g., *Neurospora, Penicillium, Tolypocladium* and *Aspergillus*, such as *A. nidulans* and *A. niger*.

The host cell disclosed herein suitable for expressing a glycosylated antibody or an antigen-binding fragment thereof is derived from multicellular organisms. Examples of invertebrate cells include plant and insect cells. Various baculovirus strains and variants thereof, as well as corresponding permissive insect host cells, have been found, which are derived from hosts such as: *Spodoptera frugiperda* (caterpillar), *Aedes aegypti* (mosquito), *Aedes albopictus* (mosquito), *Drosophila melanogaster* (fruit fly), and *Bombyx mori*. A variety of viral strains for transfection are publicly available, such as *Autographa californica* nuclear polyhedrosis virus and *Bombyx mori* nuclear polyhedrosis virus Bm-5 variant, all of which can be used in the present invention, particularly for transfecting *Spodoptera frugiperda* cells. Cells of cotton, corn, potato, soybean, petunia, tomato and tobacco may also be used as hosts.

However, the most interesting are the vertebrate cells, of which the culture (tissue culture) has become a routine practice. Examples of available mammalian host cells include SV40 transformed monkey kidney cell CV1 (COS-7, ATCC® CRL 1651); human embryonic kidney cells (293 cells or 293 cell subclone in suspension culture, Graham et al., *J. Gen. Virol.*, 36:59 (1977)); baby hamster kidney cells (B blood, ATCC® CCL 10); Chinese hamster ovary cells/-DHFR (CHO, Urlaub et al., *Proc. Natl. Acad. Sci. USA*, 77:4216 (1980)); mouse testicular support cells (TM4, Mather, *Biol. Reprod.*, 23:243-251 (1980)); monkey kidney cells (CV1_ATCC® CCL 70); sabaeus monkey kidney cells (VERO-76, ATCC® CRL-1587); human cervical cancer cells (HELA, ATCC® CCL 2); canine kidney cells (MDCK, ATCC® CCL 34); buffalo rat hepatocytes (BRL 3A, ATCC® CRL 1442); human lung cells (W138, ATCC® CCL75); human hepatocytes (Hep G2, HB 8065); mouse breast tumor cells (MMT 060562, ATCC® CCL 51); TRI cells (Mather et al., *Annals N. Y. Acad. Sci.*, 383:44-68 (1982)); MRC 5 cells; FS4 cells; and human liver cancer cells (HepG 2). In certain preferred embodiments, the host cell is a 293F cell.

The host cell is transformed with the vector for expression or cloning that produces the antibody and the antigen-binding fragment thereof and cultured in conventional nutrient media modified as appropriate for inducing promoters, selecting transformed cells, or amplifying genes encoding the sequences of interest.

The host cell disclosed herein used to produce the antibody and the antigen-binding fragment thereof can be cultured in a variety of media well known in the art. The medium may further comprise any other necessary additives at appropriate concentrations known in the art. The conditions of the medium, such as temperature, pH and the like, are those previously used for the selected host cells for expression, and are well known to those of ordinary skill in the art.

When recombinant techniques are used, the antibody can be produced intracellularly, in the periplasmic space, or directly secreted into the culture medium. If the antibody is produced intracellularly, the particle and debris of the host cells or lysed fragments are first removed, for example, by centrifugation or sonication. Carter et al., *Bio/Technology*, 10:163-167 (1992) describes a method for isolating antibodies secreted into the periplasmic space of *E. coli*. Briefly, the cell paste is thawed in the presence of uranium acetate (pH 3.5), EDTA and phenyl methyl sulphonyl fluoride (PMSF) for about 30 min or more. The cell debris is removed by centrifugation. If the antibody is secreted into the culture medium, the supernatant of the expression system is usually first concentrated using commercially available protein concentration filters, such as the AMICON® or Millipore PELLICON® ultrafiltration unit. Protease inhibitors such as PMSF may be added in any of the foregoing steps to inhibit proteolysis, as well as antibiotics to prevent the growth of adventitious contaminants.

The antibody produced from the cells can be purified by purification methods such as hydroxyapatite chromatography, gel electrophoresis, dialysis, DEAE-cellulose ion exchange chromatography, ammonium sulfate precipitation, salting out, and affinity chromatography, with affinity chromatography being a preferred purification technique. The type of antibody and the presence of the Fc domain of any immunoglobulin in the antibody determine whether protein A is suitable as an affinity ligand. Protein A can be used to purify human γ1, γ2 or γ4 heavy chain-based antibodies (Lindmark et al., *J. Immunol. Meth.*, 62:1-13 (1983)). Protein G is applicable to all murine isotypes and human γ3 (Guss et al., *EMBO J.*, 5:1567-1575 (1986)). Agarose is the most commonly used affinity ligand attachment matrix, but other matrices may also be used. Mechanically stable matrices such as controlled pore glass or poly(styrene)benzene can realize faster flow rates and shorter processing times than those of agarose. If the antibody comprises a CH3 domain, it can be purified using Bakerbond ABX. TM resin (J. T. Baker, Phillipsburg, N.J.). Other techniques for protein purification may also be determined depending on the antibody to be obtained, such as fractionation in an ion exchange column, ethanol precipitation, reverse-phase HPLC, silica gel chromatography, heparin-agarose gel chromatography based on anion or cation exchange resins (e.g., polyaspartic acid columns), chromatofocusing, SDS-PAGE, and ammonium sulfate precipitation.

After any preliminary purification procedures, the mixture comprising the antibody of interest and impurities may be treated by hydrophobic interaction chromatography at low pH, using an elution buffer at a pH of about 2.5-4.5, preferably at a low salt concentration (e.g., from about 0 to 0.25 M salt concentration).

Kits

The present application further provides a kit comprising the antibody or the antigen-binding fragment thereof. In some embodiments, the kit is used for detecting the presence or level of CD47 in a biological sample. The biological sample may comprise a cell or tissue.

In some embodiments, the kit comprises an antibody or an antigen-binding fragment thereof conjugated to a detectable label. In some embodiments, the kit comprises an unlabeled antibody, and further comprises a labeled secondary antibody capable of binding to the unlabeled antibody. The kit may further comprise a package insert and packaging separating each component in the kit.

In some embodiments, the anti-human CD47 antibody or the antigen-binding fragment thereof is ligated to a substrate or immobilized to an instrument for use in a sandwich assay such as an ELISA or immunochromatographic assay. Suitable substrates or instruments may be, for example, microwell plates and test strips.

Pharmaceutical Compositions and Methods of Treatment

The present application further provides a pharmaceutical composition comprising the antibody or the antigen-binding fragment thereof and one or more pharmaceutically acceptable carriers.

Pharmaceutically acceptable carriers for use in the pharmaceutical compositions disclosed herein may include, for example, pharmaceutically acceptable liquids, gel or solid carriers, aqueous media, non-aqueous media, antimicrobial substances, isotonic substances, buffers, antioxidants, anesthetics, suspending/dispersing agents, chelating agents, diluents, adjuvants, excipients or nontoxic auxiliary substances, other components well known in the art, or various combinations thereof.

Suitable components may include, for example, antioxidants, fillers, binders, disintegrants, buffers, preservatives, lubricants, corrigents, thickening agents, colorants, emulsifiers, or stabilizers such as carbohydrates and cyclodextrin. Suitable antioxidants may include, for example, methionine, ascorbic acid, EDTA, sodium thiosulfate, platinum, catalase, citric acid, cysteine, thioglycerol, thioglycolic acid, mercaptosorbitol, butylated hydroxyanisole, butylated hydroxytoluene and/or propyl gallate. The inclusion of one or more antioxidants, such as methionine, in the composition comprising the antibody or the antigen-binding fragment thereof disclosed herein will reduce oxidation of the antibody or the antigen-binding fragment thereof. Reduction of oxidation prevents or alleviates the reduction of binding affinity, thereby improving antibody stability and extending shelf life.

Furthermore, pharmaceutically acceptable carriers may include, for example: aqueous media such as sodium chloride injection, Ringer's solution injection, isotonic dextrose injection, sterile water for injection, or Ringer's dextrose or lactate injection; non-aqueous media such as non-volatile oils of plant sources, cottonseed oil, corn oil, sesame oil or peanut oil; antibacterial substances at a bacteria-inhibiting or fungi-inhibiting concentration; isotonic agents such as sodium chloride or glucose; buffers such as phosphate or citrate buffer; antioxidants such as sodium bisulfate; local anesthetics such as procaine hydrochloride; suspending and dispersing agents such as sodium carboxymethylcellulose, hydroxypropylmethylcellulose or polyvinylpyrrolidone; emulsifiers such as polysorbate 80 (Tween-80); chelating agents such as EDTA (ethylenediaminetetraacetic acid) or EGTA (ethylene glycol bis(2-aminoethylether)tetraacetic acid), ethanol, polyethylene glycol, propylene glycol, sodium hydroxide, hydrochloric acid, citric acid or lactic acid. Antibacterial agents as carriers may be added to the pharmaceutical composition in multi-dose containers, including phenolics or cresols, mercurials, benzyl alcohol, chlorobutanol, methylparaben and propylparaben, thimerosal, chlorophenyl methylamine and chlorophenyl ethylamine. Suitable excipients may include, for example, water, salt, glucose, glycerol or ethanol. Suitable non-toxic auxiliary substances may include, for example, emulsifiers, pH buffers, stabilizers, solubilizers, or other substances such as sodium acetate, sorbitan laurate, triethanolamine oleate or cyclodextrin.

The pharmaceutical composition may be a liquid solution, suspension, emulsion, pill, capsule, tablet, sustained release formulation or powder. Oral formulations may include standard carriers such as pharmaceutical grades of mannitol, lactose, starch, magnesium stearate, polyvinylpyrrolidone, sodium saccharin, cellulose, magnesium carbonate, and the like.

In certain embodiments, the pharmaceutical composition is formulated into an injectable composition. The injectable pharmaceutical composition may be prepared in any conventional form, for example, liquid solvents, suspending agents, emulsifiers, or solid forms suitable for the production of liquid solvents, suspending agents or emulsifiers. The formulation for injection may include ready-to-use sterile and/or pyrogen-free solutions, sterile dried solubles to be combined with a solvent prior to use such as lyophilized powders, subcutaneous tablets, ready-to-use sterile suspensions for injection, sterile dried insoluble products to be combined with a medium prior to use and sterile and/or pyrogen-free emulsions. The solvent may be aqueous or non-aqueous.

In certain embodiments, a unit dose of the formulation for injection is packaged in an ampoule, a vial or a syringe with a needle. It is well known in the art that all formulations for injection should be sterile and pyrogen-free.

In certain embodiments, a sterile lyophilized powder can be prepared by dissolving the antibody or the antigen-binding fragment thereof disclosed herein in a suitable solvent. The solvent may comprises a compound that enhances the stability of the powder or a reconstituted solution prepared from the powder, or improves other pharmacological components of the powder or reconstituted solution. Suitable excipients include, but are not limited to, water, glucose, sorbitol, fructose, corn syrup, xylitol, glycerol, glucose, brown sugar, or other suitable substances. The solvent may comprises a buffer, such as a citrate buffer, a sodium or potassium phosphate buffer or other buffers well known to those skilled in the art, and in one embodiment, the pH of the buffer is neutral. Subsequent sterile filtration of the solution, followed by lyophilization, is conducted under standard conditions well known in the art to produce the desired formulation. In one embodiment, the resulting solvent is dispensed into vials and lyophilized. Each vial may contain a single dose or multiple doses of the anti-human CD47 antibody or the antigen-binding fragment thereof, or the composition thereof. The loading per vial may be slightly higher than required for each dose or for multiple doses (e.g., a 10% excess), thereby ensuring accurate sampling and administration. The lyophilized powder may be stored in suitable conditions, such as in the range of about 4° C. to room temperature.

The lyophilized powder is reconstituted in water for injection to obtain the formulation for injection. In one embodiment, the lyophilized powder can be reconstituted by addition to sterile and pyrogen-free water or other suitable liquid carrier. The precise amount is determined according to the therapy chosen and may be determined empirically.

Also provided is a method of treatment, comprising administering to a subject in need a therapeutically effective amount of the antibody disclosed herein.

The therapeutically effective amount of the antibody disclosed herein is dependent on a variety of factors well known in the art, such as body weight, age, past medical history, current treatment, the health status and potential for cross-infection of the subject, allergies, hypersensitivity and adverse effects, as well as the route of administration and the extent of tumor progression. Those skilled in the art (e.g., physicians or veterinarians) can proportionately lower or raise the dose according to these or other conditions or requirements.

In certain embodiments, the antibody disclosed herein can be administered at a therapeutically effective dose between about 0.01 mg/kg to about 100 mg/kg. In certain embodiments, the antibody is administered at a dose of about 50 mg/kg or less, and in certain embodiments at a dose of 10 mg/kg or less, 5 mg/kg or less, 1 mg/kg or less, 0.5 mg/kg or less, or 0.1 mg/kg or less. A particular dose can be administered at intervals, such as once every day, twice or more times every day, twice or more times every month, once every week, once every two weeks, once every three weeks, once a month, or once every two or more months. In certain embodiments, the dose administered may vary over the course of treatment. For example, in certain embodiments, the initial dose administered may be higher than the subsequent dose administered. In certain embodiments, the dose administered is adjusted during the course of treatment according to the response of the subject.

The dosage regimen may be adjusted to achieve an optimal response (e.g., therapeutic response). For example, administration can be conducted in a single dose or in multiple doses over a period of time.

The antibody disclosed herein can be administered by routes of administration well known in the art, such as injection (e.g., subcutaneous injection, intraperitoneal injection, intravenous injection including intravenous drip, intramuscular injection, or intradermal injection) or non-injection administration (e.g., oral, nasal, sublingual, rectal or topical administration).

In certain embodiments, the antibody may be used for treating a disorder associated with its molecular mechanism, including a tumor and a cancer, such as non-small cell lung cancer, small cell lung cancer, renal cell carcinoma, colorectal cancer, ovarian cancer, breast cancer, pancreatic cancer, gastric cancer, bladder cancer, esophageal cancer, mesothelioma, melanoma, head and neck cancer, thyroid cancer, sarcoma, prostate cancer, glioblastoma, cervical cancer, thymus cancer, leukemia, lymphoma, myeloma, mycoses fungoids, Merkel cell carcinoma, and other hematologic malignancies, such as classical Hodgkin's lymphoma (CHL), primary mediastinal large B cell lymphoma, T-cell/histiocyte-rich B-cell lymphoma, EBV-positive and -negative PTLD and EBV-associated diffuse large B cell lymphoma (DLBCL), plasmablastic lymphoma, extranodal NK/T cell lymphoma, nasopharyngeal cancer and HHV8-associated primary effusion lymphoma, Hodgkin's lymphoma, central nervous system (CNS) tumors, such as primary CNS lymphoma, spinal axis tumor and brainstem glioma.

Method of Use

The present application further provides a method for using the antibody.

In some embodiments, the present application provides a method of treating a condition or disorder associated with the antibody mechanism in an individual, comprising administering a therapeutically effective amount of the antibody disclosed herein.

The antibody disclosed herein can be administered alone or in combination with one or more other therapeutic means or substances. For example, the antibody or the antigen-binding fragment thereof disclosed herein can be used in combination with chemotherapy, radiation therapy, surgery for cancer treatment (e.g., tumor resection), antiviral drugs, one or more anti-emetic drugs or therapies for other chemotherapy-induced complications, or any other therapeutic agents for cancer or viruses. In certain such embodiments, the antibody disclosed herein, when used in combination with one or more therapeutic substances, may be administered concurrently with the one or more therapeutic substances, and in certain such embodiments, the antibody may be administered concurrently as a part of the same pharmaceutical composition. However, the antibody "in combination" with other therapeutic substances is not necessarily administered simultaneously or in the same composition as the therapeutic substances. The definition of "in combination" in the present invention also includes that the antibody administered before or after another therapeutic substance is also considered to be "in combination" with the therapeutic substance, even if the antibody and the second substance are administered through different routes of administration. Where possible, other therapeutic substances to be used in combination with the antibody disclosed herein may be administered by reference to the method of the package insert of the therapeutic substances, by reference to the Physicians' Desk Reference 2003, 57th Ed; Medical Economics Company; ISBN: 1563634457 (November, 2002), or by reference to other methods well known in the art.

In certain embodiments, the therapeutic substance is capable of inducing or enhancing an immune response against cancer. For example, tumor vaccines can be used to induce an immune response to certain tumors or cancers. Cytokine therapy can be used to enhance the presentation of tumor antigens to the immune system. Examples of cytokine therapy include, but are not limited to, interferons such as interferon α, β and γ, colony stimulating factors such as macrophage CSF, granulocyte macrophage CSF and granulocyte CSF, interleukins such as IL-L, IL-1a, IL-2, IL 3, IL-4, IL-5, IL-6, IL-7, IL-8, IL-9, IL-10, IL-11 and IL-12, tumor necrosis factors such as TNF-α and TNF-β. Agents that inactivate immunosuppressive targets, such as PD-1 antibodies, TGF-β inhibitors, IL-10 inhibitors, and Fas ligand inhibitors, may also be used. Another group of agents include those that activate an immune response against a tumor or cancer cell, e.g., those that enhance T cell activation (e.g., T cell costimulatory signaling pathways such as CTLA-4, ICOS, OX40, 4-1BB, etc.), as well as those that enhance dendritic cell function and antigen presentation.

The following examples are intended to better illustrate the present invention and should not be construed as limiting the scope of the present invention. All of the particular compositions, materials and methods described below, completely or partially, are within the scope of the present invention. The particular compositions, materials and methods are not intended to limit the present invention, but merely to illustrate particular embodiments within the scope of the present invention. Those skilled in the art may develop equivalent compositions, materials and methods without inventive steps and without departing from the scope of the present invention. It will be appreciated that various modifications made to the methods of the present invention still fall within the scope of the present invention. The inventors intend to include such variations within the scope of the present invention.

Example 1: Acquisition of Mouse Anti-Human CD47 Monoclonal Antibody

The inventors constructed a CHO cell line over-expressing human CD47 protein, and immunized mice with the line. Spleen cells of immunized mice were taken and fused with SP2/0-AG14 cells to give hybridoma cells, and a proper amount of fused cells were transferred on a 96-well plate. The supernatant from each well was collected 10 days after the fusion, and the binding activity of the mouse antibody secreted by the hybridoma cells to human CD47 (see Example 4 for the method) and the inhibitory activity of the mouse antibody on the binding of SIRPα/CD47 (see Example 6 for the method) were measured by ELISA, to obtain a series of hybridoma cells with higher activity. Hybridoma cells with the optimal activity were selected. The heavy chain variable region cDNA sequence and the light chain variable region cDNA sequence corresponding to the secreted antibody of the hybridoma cells were obtained by sequencing. The amino acid sequence of the encoded heavy chain variable region is set forth in SEQ ID NO: 7; the amino acid sequence of the encoded light chain variable region is set forth in SEQ ID NO: 8. The heavy chain variable region and the light chain variable region of the mouse antibody were respectively ligated to the constant region of a human IgG4 heavy chain and the constant region of a κ chain to obtain a human-mouse chimeric antibody UM03-L4. The heavy chain sequence is set forth in SEQ ID NO: 9, and the light chain sequence is set forth in SEQ ID NO: 10.

The amino acid sequence of the heavy chain variable region of the hybridoma cell (i.e., the heavy chain variable region of the human-murine chimeric antibody UM03-L4) is set forth as follows:

```
SEQ ID NO: 7:
EVKLVESGGDLVQPGGSRKLSCAASGFTFSDYGMA

WIRQAPGKGPEWIAFITNLASSIYYADTVTGRFTI

SRENAKNTLYLEMSSLRSEDTAMYYCARAGDYRSF

PYWGQGTPVTVSA
```

The amino acid sequence of the light chain variable region of the hybridoma cell (i.e., the light chain variable region of the human-murine chimeric antibody UM03-L4) is set forth as follows:

```
SEQ ID NO: 8:
EILLTQSPAIIAASPGEKVTITCSASSSVNYVNWY

QQKPGSSPKIWIYGISNLASGVPARFSGSGSGTSF

SFTINSMEAEDVATYYCQQRSTFPPYTFGGGTKLE

IK
```

The amino acid sequence of the heavy chain of the human-mouse chimeric antibody UM03-L4 is set forth as follows:

```
SEQ ID NO: 9:
EVKLVESGGDLVQPGGSRKLSCAASGFTFSDYGMA

WIRQAPGKGPEWIAFITNLASSIYYADTVTGRFTI

SRENAKNTLYLEMSSLRSEDTAMYYCARAGDYRSF

PYWGQGTPVTVSAASTKGPSVFPLAPCSRSTSEST

AALGCLVKDYFPEPVTVSWNSGALTSGVHTFPAVL

QSSGLYSLSSVVTVPSSSLGTKTYTCNVDHKPSNT

KVDKRVESKYGPPCPPCPAPEFLGGPSVFLFPPKP

KDTLMISRTPEVTCVVVDVSQEDPEVQFNWYVDGV

EVHNAKTKPREEQFNSTYRVVSVLTVLHQDWLNGK

EYKCKVSNKGLPSSIEKTISKAKGQPREPQVYTLP

PSQEEMTKNQVSLTCLVKGFYPSDIAVEWESNGQP

ENNYKTTPPVLDSDGSFFLYSRLTVDKSRWQEGNV

FSCSVMHEALHNHYTQKSLSLSLGK
```

The amino acid sequence of the light chain of the human-mouse chimeric antibody UM03-L4 is set forth as follows:

```
SEQ ID NO: 10:
EILLTQSPAIIAASPGEKVTITCSASSSVNYVNWY

QQKPGSSPKIWIYGISNLASGVPARFSGSGSGTSF
```

-continued
```
SFTINSMEAEDVATYYCQQRSTFPPYTFGGGTKLE

IKRTVAAPSVFIFPPSDEQLKSGTASVVCLLNNFY

PREAKVQWKVDNALQSGNSQESVTEQDSKDSTYSL

SSTLTLSKADYEKHKVYACEVTHQGLSSPVTKSFN

RGEC
```

Example 2: Humanization of Antibodies

The sequences of the heavy chain variable region and the light chain variable region of the mouse antibody obtained in Example 1 were analyzed. The heavy chain complementarity determining regions (CDRs) comprised the following sequences: SEQ ID NO: 1, SEQ ID NO: 2 and SEQ ID NO: 3; the light chain complementarity determining regions comprised the following sequences: SEQ ID NO: 4, SEQ ID NO: 5 and SEQ ID NO: 6.

```
                              SEQ ID NO: 1
        GFTFSDYGMA

SEQ ID NO: 2
        FITNLASSIYYADTVTG

SEQ ID NO: 3
        ARAGDYRSFPY

SEQ ID NO: 4
        SASSSVNYVN

SEQ ID NO: 5
        GISNLAS

SEQ ID NO: 6
        QQRSTFPP
```

By searching a sequence database of human germline antibodies (IGMT), sequences of the human germline antibodies with high homology with heavy/light chain variable regions of the mouse antibody were respectively obtained. The framework regions of the sequences were combined with the CDRs of the mouse antibody (i.e., CDR grafting), and partial amino acids of the framework regions were reverted to finally obtain a humanized antibody UM03-C4. The heavy chain sequence of the humanized antibody is set forth in SEQ ID NO: 15, and the light chain sequence is set forth in SEQ ID NO: 16.

The heavy chain variable region sequence of humanized antibody UM03-C4 is set forth as follows:

```
                              SEQ ID NO: 13
        QVQLVESGGGVVQPGGSLRLSCAASGFTFSDYGMA

WIRQAPGKGPEWIAFITNLASSIYYADTVTGRFTI

SRDNSKNTLYLQMNSLRAEDTAVYYCARAGDYRSF

PYWGQGTLVTVSA
```

The light chain variable region sequence of humanized antibody UM03-C4 is set forth as follows:

```
                              SEQ ID NO: 14
        EIVLTQSPATLSLSPGERATLSCSASSSVNYVNWY

QQKPGQAPRILIYGISNLASGVPARFSGSGSGTDF
```

-continued
```
TLTISSLEPEDFAVYYCQQRSTFPPYTFGQGTKLE

IK
```

The heavy chain sequence of humanized antibody UM03-C4 is set forth as follows:

```
                              SEQ ID NO: 15
        QVQLVESGGGVVQPGGSLRLSCAASGFTFSDYGMA

WIRQAPGKGPEWIAFITNLASSIYYADTVTGRFTI

SRDNSKNTLYLQMNSLRAEDTAVYYCARAGDYRSF

PYWGQGTLVTVSAASTKGPSVFPLAPCSRSTSEST

AALGCLVKDYFPEPVTVSWNSGALTSGVHTFPAVL

QSSGLYSLSSVVTVPSSSLGTKTYTCNVDHKPSNT

KVDKRVESKYGPPCPPCPAPEFLGGPSVFLFPPKP

KDTLMISRTPEVTCVVVDVSQEDPEVQFNWYVDGV

EVHNAKTKPREEQFNSTYRVVSVLTVLHQDWLNGK

EYKCKVSNKGLPSSIEKTISKAKGQPREPQVYTLP

PSQEEMTKNQVSLTCLVKGFYPSDIAVEWESNGQP

ENNYKTTPPVLDSDGSFFLYSRLTVDKSRWQEGNV

FSCSVMHEALHNHYTQKSLSLSLGK
```

The light chain sequence of humanized antibody UM03-C4 is set forth as follows:

```
                              SEQ ID NO: 16
        EIVLTQSPATLSLSPGERATLSCSASSSVNYVNWY

QQKPGQAPRILIYGISNLASGVPARFSGSGSGTDF

TLTISSLEPEDFAVYYCQQRSTFPPYTFGQGTKLE

IKRTVAAPSVFIFPPSDEQLKSGTASVVCLLNNFY

PREAKVQWKVDNALQSGNSQESVTEQDSKDSTYSL

SSTLTLSKADYEKHKVYACEVTHQGLSSPVTKSFN

RGEC
```

Example 3: Preparation of Antibodies

The cDNA sequences encoding the heavy chain and light chain of UM03-L4 are set forth in SEQ ID NO: 11 and SEQ ID NO: 12, respectively; the cDNA sequences encoding the heavy chain and light chain of UM03-C4 are set forth in SEQ ID NO: 17 and SEQ ID NO: 18, respectively.

```
The cDNA encoding the UM03-L4
heavy chain (SEQ ID NO: 11):
GAGGTGAAGCTGGTGGAGAGCGGCGGCGACCTGGT

GCAGCCAGGAGGATCCAGAAAGCTGAGCTGTGCCG

CCAGCGGCTTCACATTCAGCGACTACGGCATGGCC

TGGATCAGGCAGGCCCCTGGCAAGGGCCCCGAGTG

GATCGCCTTCATCACCAATCTGGCCTCCTCCATCT

ACTACGCCGACACAGTGACCGGCAGGTTCACCATC
```

-continued

AGCAGAGAGAACGCCAAGAACACACTGTACCTGGA

GATGTCCTCCCTGAGAAGCGAGGACACAGCCATGT

ACTACTGTGCCAGAGCCGGCGACTACAGGAGCTTC

CCCTACTGGGGCCAGGGCACACCTGTGACCGTGTC

CGCCGCTAGCACAAAGGGCCCCAGCGTGTTTCCTC

TGGCCCCCTGCAGCAGAAGCACCAGCGAGTCCACC

GCCGCCCTGGGATGCCTGGTGAAGGACTACTTCCC

TGAGCCCGTGACAGTGAGCTGGAATAGCGGCGCCC

TGACAAGCGGCGTGCACACCTTTCCTGCCGTGCTG

CAGTCCAGCGGCCTGTACAGCCTGAGCAGCGTGGT

GACAGTGCCTAGCTCCTCCCTGGGCACAAAGACAT

ACACCTGCAATGTGGACCACAAGCCCAGCAACACA

AAGGTGGACAAGAGAGTGGAGAGCAAGTACGGCCC

TCCTTGTCCCCCTTGTCCTGCCCCTGAGTTTCTGG

GCGGCCCCTCCGTGTTTCTGTTTCCTCCCAAGCCT

AAGGATACCCTGATGATCTCCAGAACCCCCGAGGT

GACCTGTGTGGTGGTGGATGTGAGCCAGGAGGACC

CCGAGGTGCAGTTCAACTGGTACGTGGACGGCGTG

GAGGTGCACAATGCCAAGACCAAGCCCAGGGAGGA

GCAGTTTAACTCCACATACAGGGTGGTGTCCGTGC

TGACCGTGCTGCACCAGGACTGGCTGAATGGCAAG

GAGTACAAGTGTAAGGTGAGCAACAAGGGCCTGCC

TAGCTCCATCGAGAAGACCATCTCCAAGGCCAAGG

GCCAGCCTAGGGAGCCCCAGGTGTACACACTGCCT

CCCAGCCAGGAGGAGATGACAAAGAACCAGGTGAG

CCTGACATGCCTGGTGAAAGGCTTCTACCCTTCCG

ACATCGCCGTGGAGTGGGAGTCCAACGGCCAGCCT

GAGAACAATTACAAGACAACCCCCCCCGTGCTGGA

TTCCGACGGCAGCTTTTTCCTGTACTCCAGACTGA

CCGTGGACAAGAGCAGATGGCAGGAGGGCAATGTG

TTTAGCTGTTCCGTGATGCACGAGGCCCTGCACAA

TCACTACACACAGAAGTCCCTGAGCCTGAGCCTGG

GCAAA

The cDNA encoding the UM03-L4
light chain (SEQ ID NO: 12):
GAGATCCTGCTGACCCAGAGCCCCGCCATCATCGC

CGCCAGCCCTGGAGAGAAGGTGACCATCACATGTT

CCGCCAGCAGCAGCGTGAATTACGTGAACTGGTAT

CAACAGAAGCCTGGCAGCAGCCCTAAGATCTGGAT

CTACGGCATCTCCAACCTGGCCTCCGGCGTGCCTG

CCAGGTTCAGCGGAAGCGGCAGCGGCACCAGCTTC

-continued

AGCTTCACAATCAATAGCATGGAGGCCGAGGATGT

GGCCACATACTACTGTCAGCAGAGATCCACATTCC

CTCCCTACACATTCGGCGGCGGCACCAAGCTGGAG

ATCAAGCGTACGGTGGCTGCACCATCTGTCTTCAT

CTTCCCGCCATCTGATGAGCAGTTGAAATCTGGAA

CTGCCTCTGTTGTGTGCCTGCTGAATAACTTCTAT

CCCAGAGAGGCCAAAGTACAGTGGAAGGTGGATAA

CGCCCTCCAATCGGGTAACTCCCAGGAGAGTGTCA

CAGAGCAGGACAGCAAGGACAGCACCTACAGCCTC

AGCAGCACCCTGACGCTGAGCAAAGCAGACTACGA

GAAACACAAAGTCTACGCCTGCGAAGTCACCCATC

AGGGCCTGAGTTCGCCCGTCACAAAGAGCTTCAAC

AGGGGAGAGTGT

The cDNA encoding the UM03-C4
heavy chain (SEQ ID NO: 17):
CAGGTCCAGCTGGTCGAGTCAGGCGGCGGCGTCGT

GCAGCCTGGAGGATCACTGAGACTGAGCTGCGCAG

CCAGCGGCTTCACATTCAGCGACTACGGCATGGCC

TGGATCAGACAGGCACCCGGCAAAGGGCCAGAGTG

GATTGCTTTCATCACCAACCTGGCCAGCAGCATCT

ACTACGCCGACACCGTGACAGGCAGATTCACCATC

AGCAGAGACAACAGCAAGAACACACTGTACCTGCA

GATGAACAGCCTGCGCGCCGAGGACACCGCCGTGT

ACTACTGCGCCAGGGCCGGAGACTACAGATCCTTT

CCCTACTGGGGCAGGGAACCCTGGTGACCGTCAG

CGCCGCTAGCACCAAGGGCCCATCGGTCTTCCCCC

TGGCGCCCTGCTCCAGGAGCACCTCCGAGAGCACA

GCCGCCCTGGGCTGCCTGGTCAAGGACTACTTCCC

CGAACCGGTGACGGTGTCGTGGAACTCAGGCGCCC

TGACCAGCGGCGTGCACACCTTCCCGGCTGTCCTA

CAGTCCTCAGGACTCTACTCCCTCAGCAGCGTGGT

GACCGTGCCCTCCAGCAGCTTGGGCACGAAGACCT

ACACCTGCAACGTAGATCACAAGCCCAGCAACACC

AAGGTGGACAAGAGAGTTGAGTCCAAATATGGTCC

CCCATGCCCACCATGCCCAGCACCTGAGTTCCTGG

GGGGACCATCAGTCTTCCTGTTCCCCCCAAAACCC

AAGGACACTCTCATGATCTCCCGGACCCCTGAGGT

CACGTGCGTGGTGGTGGACGTGAGCCAGGAAGACC

CCGAGGTCCAGTTCAACTGGTACGTGGATGGCGTG

GAGGTGCATAATGCCAAGACAAAGCCGCGGGAGGA

GCAGTTCAACAGCACGTACCGTGTGGTCAGCGTCC

TCACCGTCCTGCACCAGGACTGGCTGAACGGCAAG

-continued

```
GAGTACAAGTGCAAGGTCTCCAACAAAGGCCTCCC

GTCCTCCATCGAGAAAACCATCTCCAAAGCCAAAG

GGCAGCCCCGAGAGCCACAGGTGTACACCCTGCCC

CCATCCCAGGAGGAGATGACCAAGAACCAGGTCAG

CCTGACCTGCCTGGTCAAAGGCTTCTACCCCAGCG

ACATCGCCGTGGAGTGGGAGAGCAATGGGCAGCCG

GAGAACAACTACAAGACCACGCCTCCCGTGCTGGA

CTCCGACGGCTCCTTCTTCCTCTACAGCAGGCTAA

CCGTGGACAAGAGCAGGTGGCAGGAGGGGAATGTC

TTCTCATGCTCCGTGATGCATGAGGCTCTGCACAA

CCACTACACACAGAAGAGCCTCTCCCTGTCTCTGG

GTAAA
```

The cDNA encoding the UM03-C4
light chain (SEQ ID NO: 18):
```
GAGATTGTGCTGACCCAGAGCCCCGCCACACTGAG

TCTGAGTCCCGGCGAGAGAGCAACACTGAGTTGTA

GCGCCAGCAGTAGTGTGAACTACGTGAACTGGTAT

CAGCAGAAGCCTGGACAGGCTCCCAGAATCCTGAT

CTACGGCATCTCCAACCTGGCCAGCGGAGTGCCCG

CCAGATTCAGCGGAAGTGGCAGCGGGACAGACTTC

ACCCTGACCATCAGCAGCCTGGAACCCGAGGATTT

CGCCGTGTACTACTGCCAGCAGAGAAGCACCTTCC

CCCCCTATACATTTGGCCAGGGAACCAAGCTGGAA

ATCAAACGTACGGTGGCTGCACCATCTGTCTTCAT

CTTCCCGCCATCTGATGAGCAGTTGAAATCTGGAA

CTGCCTCTGTTGTGTGCCTGCTGAATAACTTCTAT

CCCAGAGAGGCCAAAGTACAGTGGAAGGTGGATAA

CGCCCTCCAATCGGGTAACTCCCAGGAGAGTGTCA

CAGAGCAGGACAGCAAGGACAGCACCTACAGCCTC

AGCAGCACCCTGACGCTGAGCAAAGCAGACTACGA

GAAACACAAAGTCTACGCCTGCGAAGTCACCCATC

AGGGCCTGAGTTCGCCCGTCACAAAGAGCTTCAAC

AGGGGAGAGTGT
```

After the cDNA sequences were ligated to the sequences encoding the signal peptide, the ligated sequences were separately cloned into the mammalian cell expression vector pcDNA3.4. The heavy chain expression plasmid and the light chain expression plasmid were transfected into HEK293 cells using Lipofectamine 2000 transfection reagent (INVITROGEN™) in a 2:1 molar ratio and cultured at 37° C. at 5% carbon dioxide for 7 days. The culture supernatant was collected, and the antibody in the supernatant was purified by Protein A affinity chromatography. The purified antibody was dialyzed against PBS, lyophilized, concentrated and preserved at –20° C.

Example 4: Binding of Antibodies to CD47 Protein

A 96-well high affinity plate was coated with a 1 μg/mL human CD47 protein solution at 100 μL/well and shaken overnight at 4° C. The next day, the plate was washed 3 times with 300 μL of PBST (Tween 20: 0.5‰), then blocked with 5% BSA/PBS at 100 μL/well for 2 h, and shaken at room temperature. The plate was then washed with 300 μL of PBST 3 times. The antibody samples prepared with PBS were serially diluted, added to a 96-well plate at 100 μL/well and shaken for 1 h at room temperature. The plate was then washed with 300 μL of PBST 3 times. A secondary goat anti-mouse IgG HRP or goat anti-human IgG HRP solution was prepared, added to a 96-well plate at 100 μL/well and shaken for 1 h at room temperature. The plate was then washed with 300 μL of PBST 4 times. TMB was added at 100 μL/well for 20 min of chromogenesis. The chromogenesis was terminated by adding 0.6 N $H_2SO_4$ at 100 μL/well and the $OD_{450\ nm}$ was detected.

As the results of the detection shown in FIG. 1, the $EC_{50}$ for binding of the chimeric antibody UM03-L4 to human CD47 was 0.2499 μg/mL, and the $EC_{50}$ for binding of the humanized antibody UM03-C4 to human CD47 was 0.1687 μg/mL.

Example 5: Binding of Antibodies to Human Tumor Cells Highly Expressing Human CD47

Figure 2A:
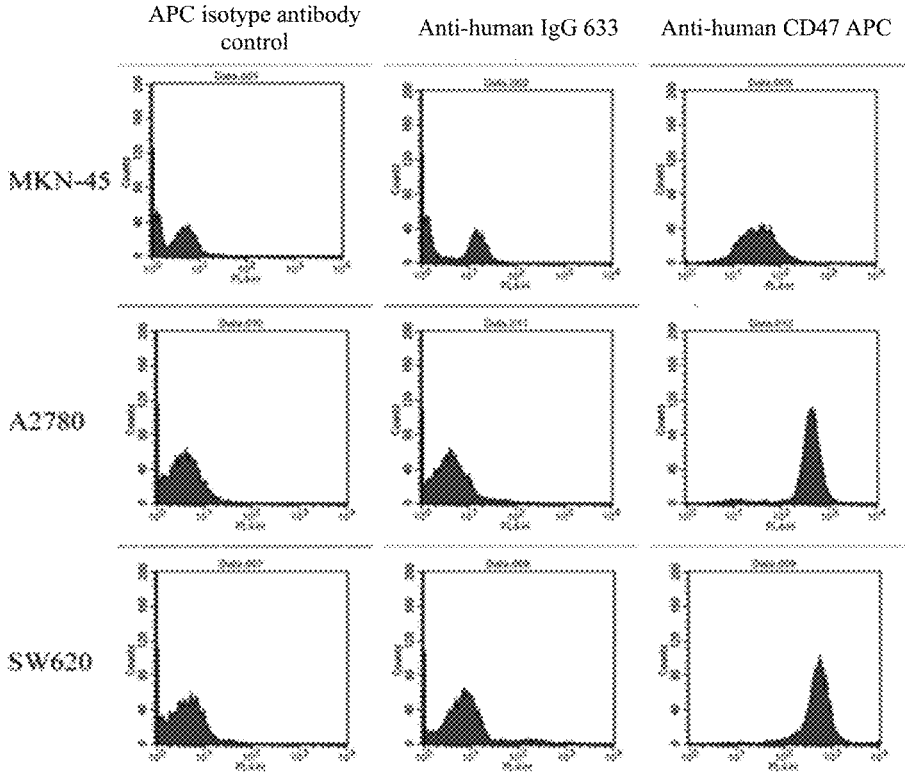
In FIG. 2A, MKN-45, A2780 and SW620 are CD47 positive cells.

The gastric cancer cell line MKN-45, the ovarian cancer cell line A2780 and the colon cancer cell line SW620 (ATCC®) are human-derived tumor cells highly expressing CD47. First, the inventors verified the expression of CD47 in the above 3 cell lines using flow cytometry. Serially diluted solutions of anti-human CD47 detection antibody (eBioscience, 17-0479-42) and APC isotype (eBioscience, 17-4714-41), anti-huIgG 633 (life technologies, A21091) were prepared with PBS to formulate 2× working solutions at final concentrations. The three tumor cells were collected, washed with PBS once, counted, and diluted to $4 \times 10^6$/mL cell suspension. For each cell line, 50 μL of the antibody working solution was added into 50 μL of cell suspension, and the mixture was incubated at 4° C. in the dark for 30 min. After washing twice with PBS, a corresponding fluorescence-labeled secondary antibody (anti-huIgG 633) was added, and the mixture was incubated for 30 min at 4° C. in the dark, washed twice with PBS, and suspended with 400 μL of FACS buffer. The binding of the antibodies to the cells was detected by a flow cytometer. The results showed that all three cells were CD47-positive cells (FIG. 2A).

Figure 2B:
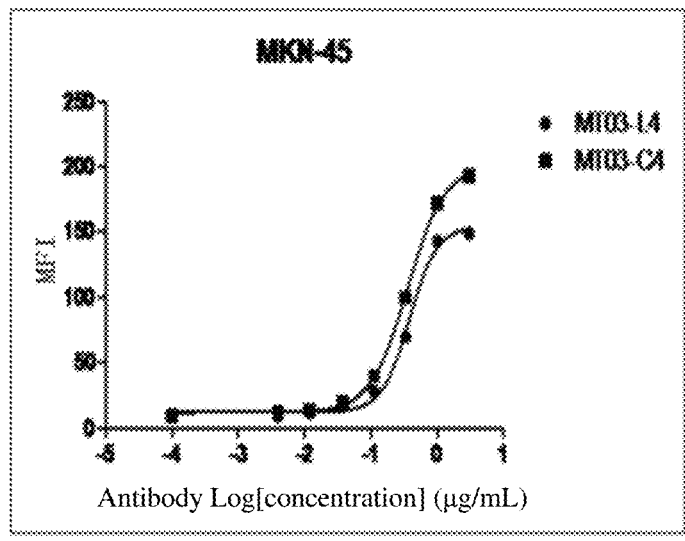
FIG. 2B illustrates that the antibodies UM03-L4 and UM03-C4 disclosed herein had strong binding to MKN-45, A2780 and SW620.
Figure 2B:
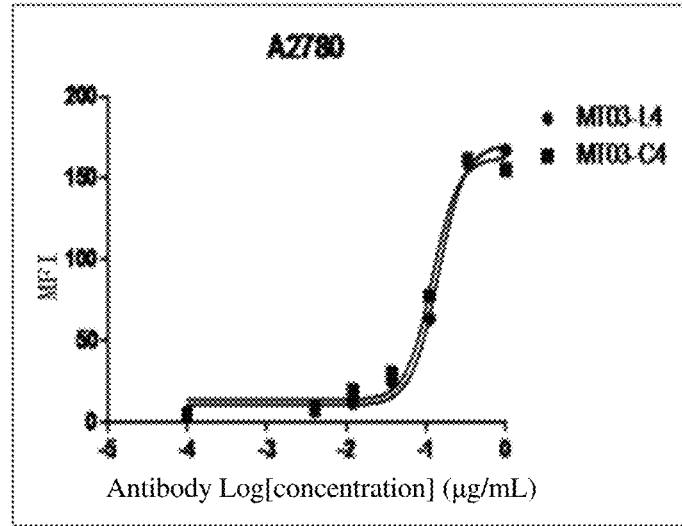
Figure 2B:
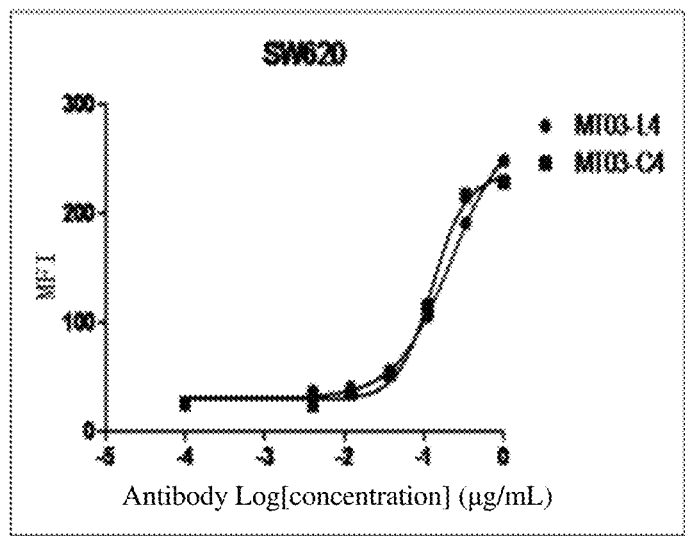

The inventors examined the binding of the chimeric antibody UM03-L4 and the humanized antibody UM03-C4 to the above 3 tumor cell lines. The method is the same as above. As shown in FIG. 2B, the results showed that both the chimeric antibody UM03-L4 and the humanized antibody UM03-C4 bound to the three human tumor cells highly expressing human CD47. The results are summarized in Table 1.

Figures 2C, 3:
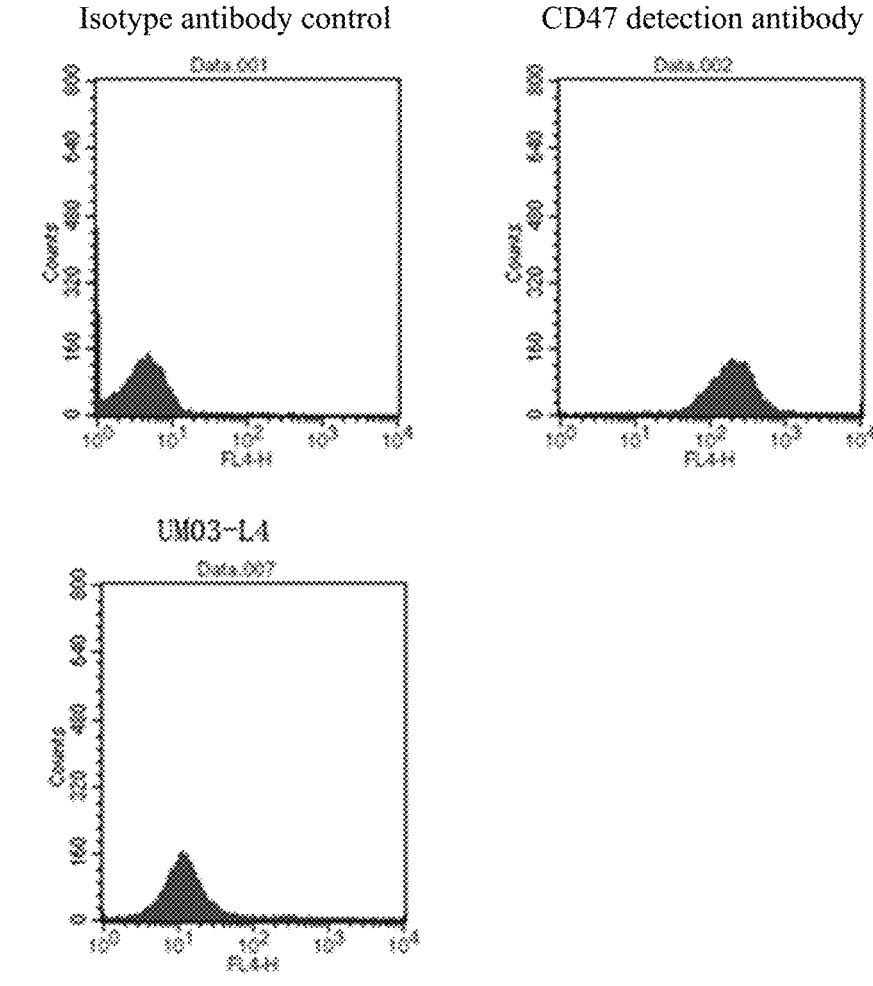
FIG. 2C illustrates the binding of the anti-human CD47 antibody disclosed herein to mouse tumor cell MC-38 highly expressing murine CD47, suggesting only very weak binding of UM03-L4 to mouse CD47.
FIG. 3 illustrates that the anti-human CD47 antibody disclosed herein can inhibit the binding of CHO-CD47 cell to SIRPα protein.

Similarly, the inventors detected the binding of the antibody UM03-L4 to mouse tumor cell MC-38 highly expressing murine CD47, and found no binding of UM03-L4 to mouse CD47, as shown in FIG. 2C, where the isotype antibody control was APC isotype (BIOLEGEND®, 400511) and the CD47 detection antibody was anti-murine CD47 detection antibody (BIOLEGEND®, 127513).

TABLE 1

| EC$_{50}$ for binding of humanized antibody UM03-C4 to human tumor cells (μg/mL) | | |
| --- | --- | --- |
| | UM03-L4 | UM03-C4 |
| MKN-45 | 0.3811 | 0.3544 |
| A2780 | 0.142 | 0.1191 |
| SW620 | 0.2163 | 0.1262 |

Example 6: Antibody Inhibition Against Binding of CHO-CD47 Cells to SIRPα Protein A stable CHO cell line overexpressing human CD47 was first constructed. Serially diluted antibody solutions were prepared with PBS to formulate 2× working solutions at final concentrations. CHO-CD47 cells were collected, centrifuged and resuspended in culture medium. The density was adjusted to $4 \times 10^6$/mL. 50 μL of antibody working solution was added into 50 μL of cell suspension, and the mixture was incubated at 4° C. in the dark for 30 min. After washing twice with PBS, 100 μL of 4 μg/mL SIRPα-mFc (Acrobiosystems) or PBS was added and the mixture was incubated at 4° C. for 30 min. After washing twice with PBS, a corresponding fluorescence-labeled secondary antibody was added, and the mixture was incubated for 30 min at 4° C. in the dark, washed twice with PBS, and suspended with 400 μL of FACS buffer. The binding of the antibodies to the cells was detected by a flow cytometer.

As shown in FIG. 3, the SIRPα protein can bind to CHO-CD47 cells, and the binding can be inhibited by the chimeric antibody UM03-L4 or the humanized antibody UM03-C4, with IC$_{50}$ values of 3.383 μg/mL and 2.398 μg/mL, respectively.

Example 7: Binding of Antibody to Human Erythrocytes and Agglutination Effect on Human Erythrocytes The inventors examined the binding of the chimeric antibody UM03-L4 and the humanized antibody UM03-C4 as well as a positive control antibody Hu5F9 (U.S. Pat. No. 9,017,675B2 and PLoS ONE 2015, 10(9): e0137345) to human erythrocytes as well as the agglutination effect on human erythrocytes. Erythrocytes were first isolated from the peripheral blood of volunteers and suspended in physiological saline to obtain an erythrocyte suspension with a concentration of 2%. Serially diluted antibody solutions were prepared with PBS to formulate 2× working solutions at final concentrations. 50 μL of the antibody working solution was added into 50 μL of erythrocyte suspension, and the mixture was incubated at 4° C. in the dark for 60 min. After washing twice with PBS, a corresponding fluorescence-labeled secondary antibody was added, and the mixture was incubated for 30 min at 4° C. in the dark, washed twice with PBS, and suspended with 400 μL of FACS buffer. The binding of the antibodies to the erythrocytes was detected by a flow cytometer. For erythrocyte agglutination detection, 50 μL of the antibody working solution was also added into 50 μL of erythrocyte suspension. The mixture was placed on a 96-well round bottom plate, let stand at room temperature for 2 h, observed and photographed.

Figure 4A:
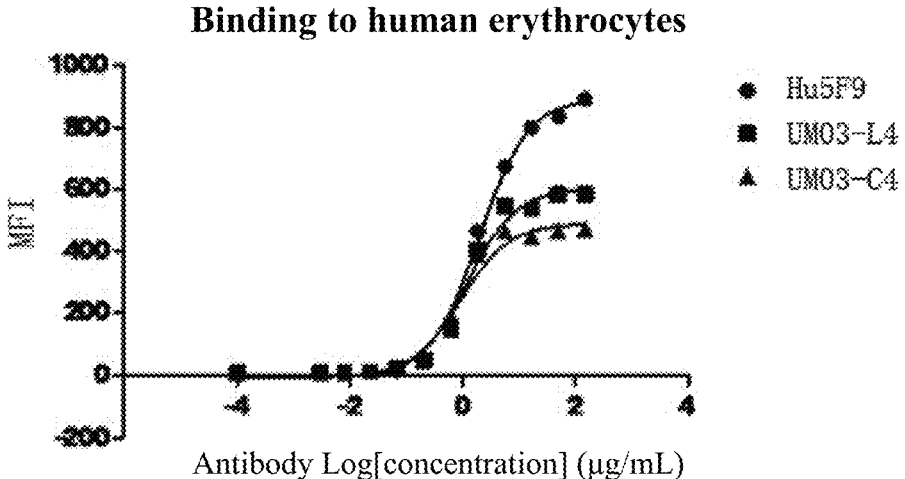
FIG. 4A and FIG. 4B illustrate the binding of the anti-human CD47 antibody disclosed herein to human erythrocytes and the agglutination effect on human erythrocytes.
Figure 4B:
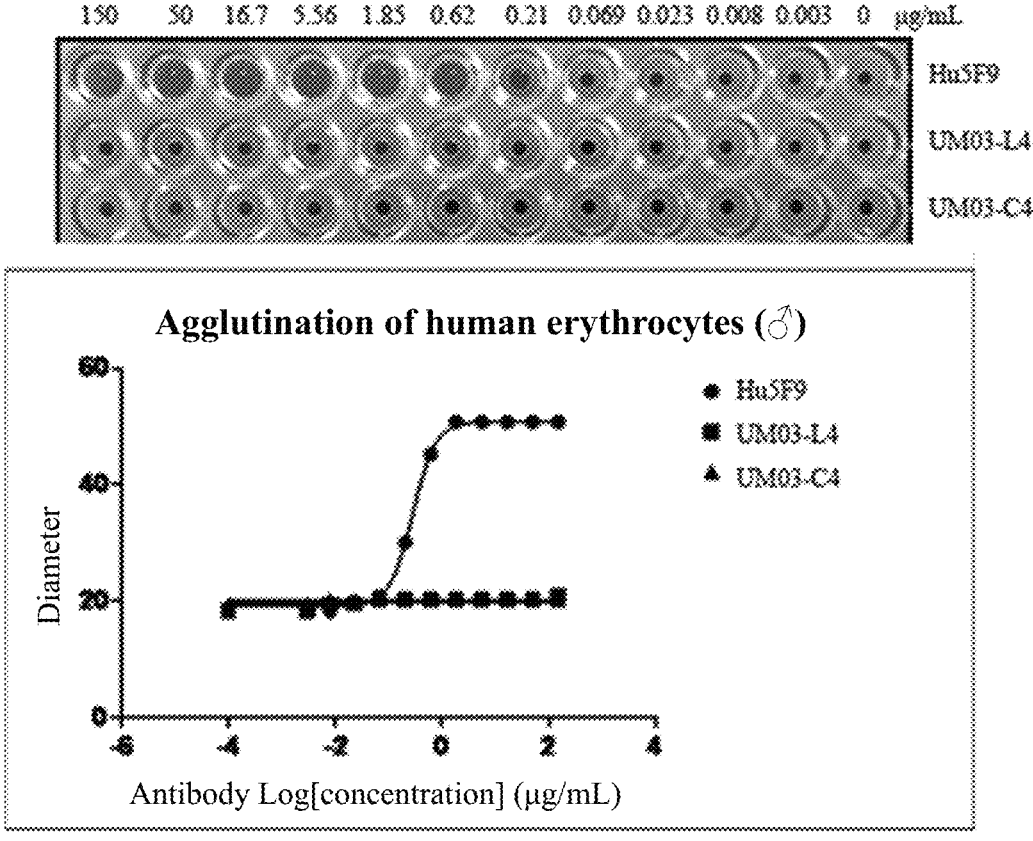

As shown in FIG. 4A, the chimeric antibody UM03-L4 and the humanized antibody UM03-C4 bound to human erythrocytes with EC$_{50}$ values of 1.21 μg/mL and 0.93

μg/mL, respectively, and plateaus of 586 and 473, respectively. The EC$_{50}$ and the plateau of the positive control antibody Hu5F9 to human erythrocytes were 1.954 μg/mL and 892, respectively. As shown in FIG. 4B, the chimeric antibody UM03-L4 and the humanized antibody UM03-C4 had little agglutination effect on human erythrocytes, and the positive control antibody had strong agglutination effect on human erythrocytes.

Figure 5A:
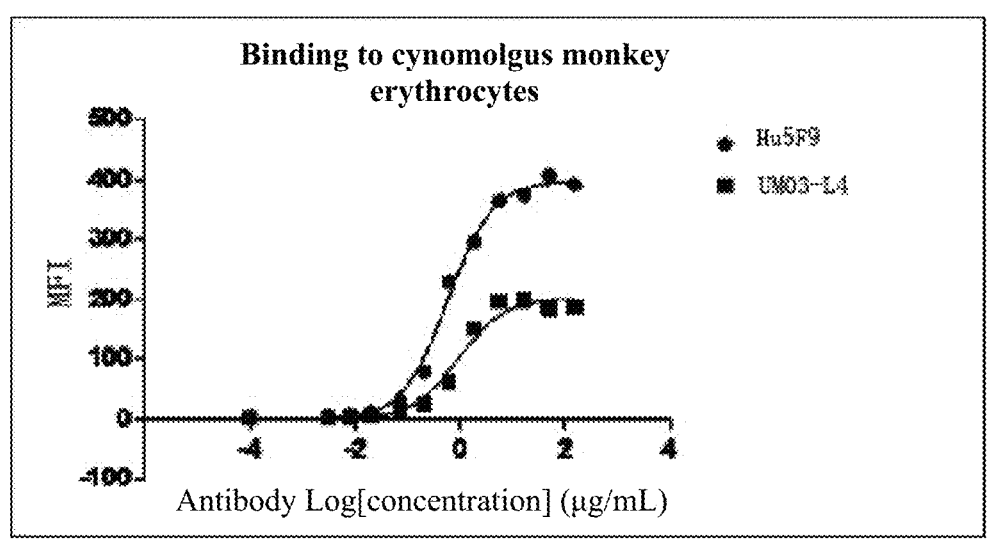
FIG. 5A illustrates the binding of the anti-human CD47 antibody UM03-L4 disclosed herein and the positive control antibody to monkey erythrocytes.
Figure 5B:
FIG. 5B illustrates that the anti-human CD47 antibody UM03-L4 disclosed herein had little agglutination effect on monkey erythrocytes, and the positive control antibody had strong agglutination effect on monkey erythrocytes.
Figure 5B:
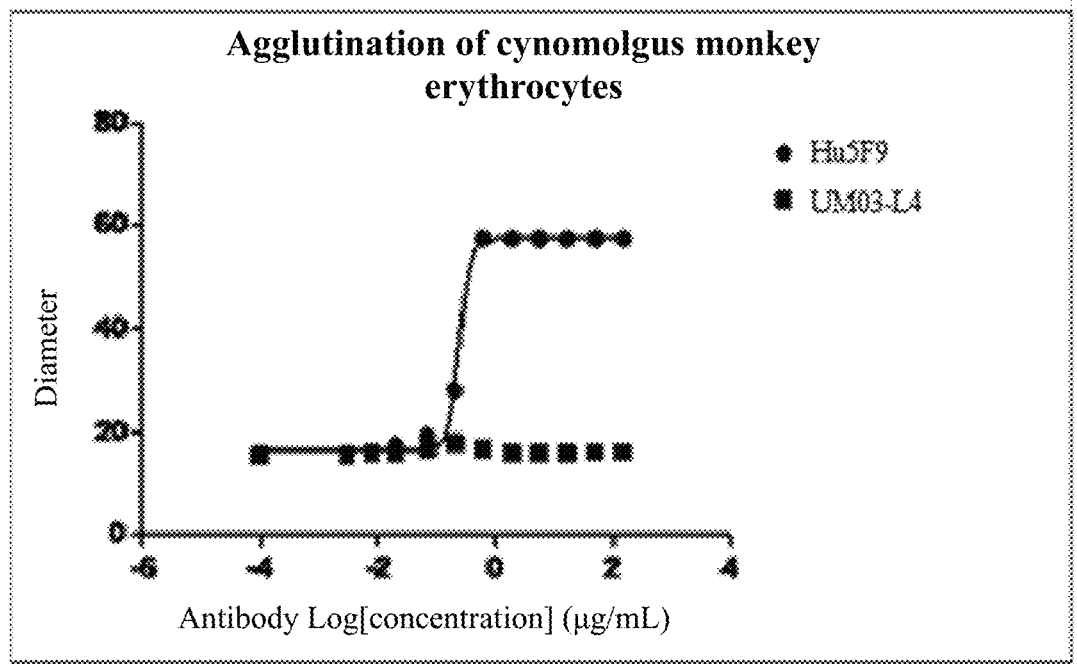

Example 8: Binding of Antibodies to Monkey Erythrocytes and Agglutination Effect on Monkey Erythrocytes Similarly, the inventors examined the binding of the chimeric antibody UM03-L4 and the positive control antibody Hu5F9 to monkey erythrocytes as well as the agglutination effect on monkey erythrocytes, with the same method for human erythrocytes. As shown in FIG. 5A, the chimeric antibody UM03-L4 and the positive control antibody bound to monkey erythrocytes with EC$_{50}$ values of 0.9070 μg/mL and 0.5860 μg/mL, respectively, and plateaus of 186 and 392, respectively. Similarly, FIG. 5B illustrates that the chimeric antibody UM03-L4 had little agglutination effect on monkey erythrocytes, and that the positive control antibody had a strong agglutination effect on monkey erythrocytes.

Example 9: Antigen-Antibody Affinity Assay

Figure 6:
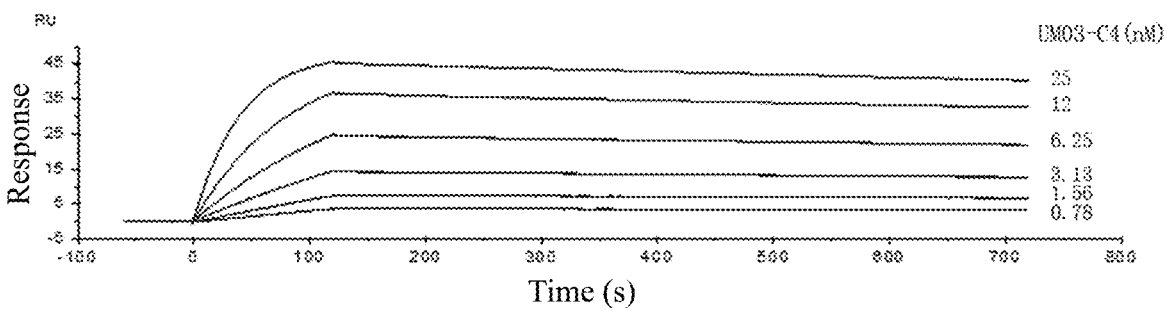
FIG. 6 illustrates the detection of the antigen-antibody affinity of the anti-human CD47 antibody disclosed herein.

The affinity of antigen-antibody binding was measured by SPR (surface plasma resonance). Briefly, UM03-C4 at a concentration of 4 μg/mL was co-incubated with a protein A sensor chip (GE, Cat #29127556) for 30 s for antibody capture. In the antigen binding phase, the binding between serially diluted CD47 protein as the mobile phase and the UM03-C4 antibody captured on a sensor chip was conducted for 120 s. During the dissociation phase, elution was continued for 360 s with HBS-EP buffer. The binding of CD47 to the antibody on the sensor chip was quantitatively determined using Biacore T200 (GE Healthcare). As shown in Table 2 and FIG. 6, the affinity of UM03-C4 was 0.4 nM.

TABLE 2

| Affinity and kinetic data of UM03-C4 for CD47 | | | | |
| --- | --- | --- | --- | --- |
| Receptor | Ligand | Ka (1/Ms) | Kd (1/s) | KD (M) |
| CD47 | UM03–C4 | 1.02E+06 | 1.933E–04 | 1.90E–10 |

Example 10: Mouse Tumor Efficacy Model

Daudi cells (ATCC®, human lymphoma cells) that are tumor cells highly expressing CD47 were inoculated subcutaneously in female NCG mice at an amount of $6 \times 10^6$ cells/mouse. After tumors grew to about 150 mm$^3$, the mice were divided into 6 groups. Mice were intravenously received 2.5 mg/kg of UM03-C4 antibody, 5 mg/kg of UM03-C4 antibody, 10 mg/kg of UM03-C4 antibody, Hu5F9 (5 mg/kg) as positive antibody, and 5 mg/kg of IgG1 isotype control antibody, respectively. The administration was performed once every 3 days for a total of 4 doses.

Figure 7:
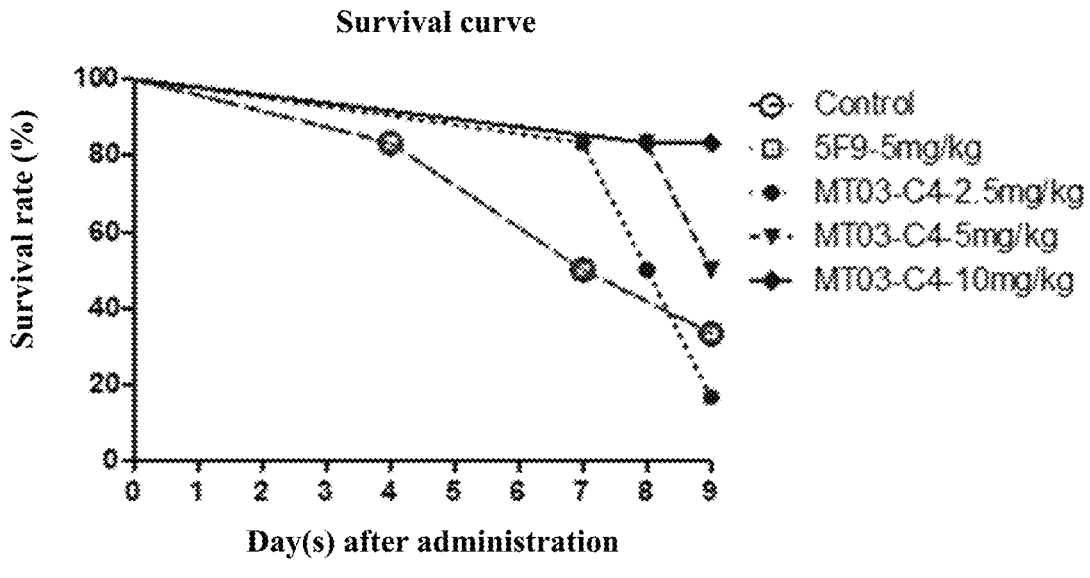
FIG. 7 illustrates the antitumor effect of the anti-human CD47 antibody disclosed herein in mice.

As shown in FIG. 7, since the model is an advanced tumor model, mice in the positive control antibody Hu5F9 group failed to reach a longer survival as compared to mice in the control group, while the UM03-C4 antibody treatment group showed clear efficacy at various doses.

Example 11: Drug Metabolism in Cynomolgus Monkeys

Figure 8:
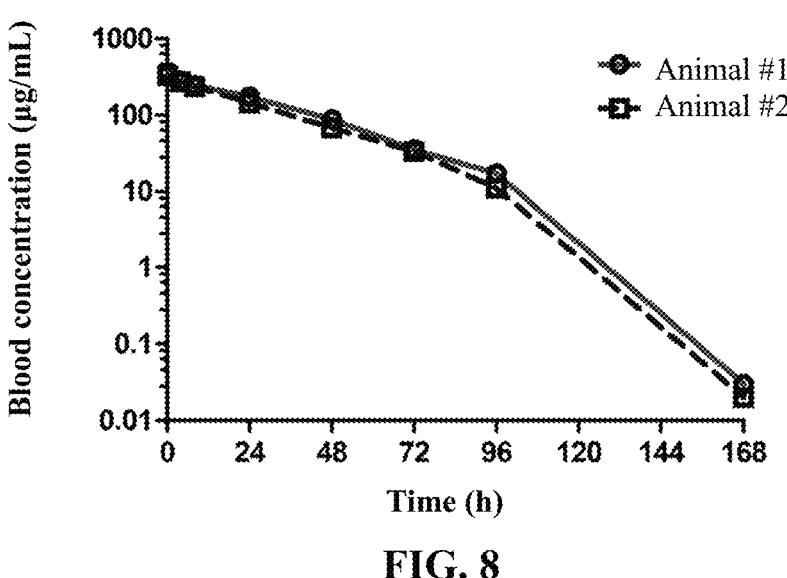
FIG. 8 illustrates the drug metabolism test of the anti-human CD47 antibody disclosed herein in cynomolgus monkeys.

Cynomolgus monkeys (n=2) were administered intravenously with UM03-C4 at a dose of 15 mg/kg. Blood was collected pre-dose, and at 0, 0.25, 4, 8, 24, 48, 72, 96, 144, 192, 240 and 336 hours post-dose, and blood concentration was measured by ELISA and plotted versus the time of administration. The results are shown in FIG. 8. Pharmacokinetic parameters were also calculated and the results are shown in Table 1. In this experiment, moderate anemia and no significant thrombocytopenia were observed in the cynomolgus monkeys.

TABLE 3

| | Pharmacokinetic parameters of UM03-C4 in cynomolgus monkeys (15 mg/kg, n = 2) | | | | | |
|---|---|---|---|---|---|---|
| | Half life (h) | Peak concentration (µg/mL) | AUC exposure (h*µg/mL) | Apparent volume of distribution (mL/kg) | Apparent clearance (mL/h/kg) | Average retention time (h) |
| UM03-C4 average | 8.85 | 345.3 | 10765.2 | 17.87 | 1.40 | 29.11 |

The above description is only preferred embodiments of the present invention and is not intended to limit the present invention in any way. Any equivalent substitutions, modifications and other variations to the technical schemes and technical contents disclosed herein made by those skilled in the art without departing from the scope of the technical schemes of the present invention shall still fall within the protection scope of the present invention without departing from the technical schemes of the present invention.

The invention claimed is:

1. An anti-human CD47 antibody or an antigen-binding fragment thereof comprising the following heavy chain complementarity determining regions:
   - a VH CDR1 comprising an amino acid sequence set forth in SEQ ID NO: 1;
   - a VH CDR2 comprising an amino acid sequence set forth in SEQ ID NO: 2; and
   - a VH CDR3 comprising an amino acid sequence set forth in SEQ ID NO: 3;
   - and the following light chain complementarity determining regions:
   - a VL CDR1 comprising an amino acid sequence set forth in SEQ ID NO: 4;
   - a VL CDR2 comprising an amino acid sequence set forth in SEQ ID NO: 5; and
   - a VL CDR3 comprising an amino acid sequence set forth in SEQ ID NO: 6.

2. The antibody or the antigen-binding fragment thereof according to claim 1, wherein the anti-human CD47 antibody or the antigen-binding fragment thereof is an scFv, an scFv dimer, a BsFv, a dsFv, a dsFv2, a dsFv-dsFv', an Fv fragment, an Fab, an Fab', an F(ab')2, or a ds bifunctional antibody.

3. The antibody or the antigen-binding fragment thereof according to claim 1, wherein the anti-human CD47 antibody or the antigen-binding fragment thereof has a heavy chain variable region comprising an amino acid sequence set forth in SEQ ID NO: 7; and/or
   the anti-human CD47 antibody or the antigen-binding fragment thereof has a light chain variable region comprising an amino acid sequence set forth in SEQ ID NO: 8; or
   the anti-human CD47 antibody or the antigen-binding fragment thereof has a heavy chain variable region comprising an amino acid sequence set forth in SEQ ID NO: 13; and/or the anti-human CD47 antibody or the antigen-binding fragment thereof has a light chain variable region comprising an amino acid sequence set forth in SEQ ID NO: 14.

4. The antibody or the antigen-binding fragment thereof according to claim 1, wherein the anti-human CD47 antibody or the antigen-binding fragment thereof has a heavy chain comprising an amino acid sequence set forth in SEQ ID NO: 9; and/or the anti-human CD47 antibody or the antigen-binding fragment thereof has a light chain comprising an amino acid sequence set forth in SEQ ID NO: 10; or
   the anti-human CD47 antibody or the antigen-binding fragment thereof has a heavy chain comprising an amino acid sequence set forth in SEQ ID NO: 15; and/or the anti-human CD47 antibody or the antigen-binding fragment thereof has a light chain comprising an amino acid sequence set forth in SEQ ID NO: 16.

5. An isolated polynucleotide encoding the antibody or the antigen-binding fragment thereof according to claim 1,
   wherein the polynucleotide comprises a nucleotide sequence set forth in SEQ ID NO: 11 and
   the polynucleotide comprises a nucleotide sequence set forth in SEQ ID NO: 12; or
   the polynucleotide comprises a nucleotide sequence set forth in SEQ ID NO: 17 and the polynucleotide comprises a nucleotide sequence set forth in SEQ ID NO: 18.

6. A vector comprising the isolated polynucleotide according to claim 5.

7. A host cell comprising the vector according to claim 6.

8. A method for preparing the anti-human CD47 antibody or the antigen-binding fragment thereof according to claim 1, comprising culturing a host cell in a condition for expressing an isolated polynucleotide encoding said antibody or the antigen-binding fragment thereof.

9. A kit comprising the anti-human CD47 antibody or the antigen-binding fragment thereof according to claim 1.

10. A pharmaceutical composition comprising the anti-human CD47 antibody or the antigen-binding fragment thereof according to claim 1 and a pharmaceutically acceptable carrier.

11. The antibody or the antigen-binding fragment thereof according to claim 2, wherein the anti-human CD47 antibody or the antigen-binding fragment thereof further comprises a human heavy chain constant region and/or a human light chain constant region.

12. The antibody or the antigen-binding fragment thereof according to claim 11, wherein the human heavy chain constant region is selected from a heavy chain constant region of human IgG1, IgG2, IgG3 and IgG4, and the human light chain constant region is selected from a light chain constant region of human IgG1, IgG2, IgG3 and IgG4.

13. The antibody or the antigen-binding fragment thereof according to claim 11, wherein the human heavy chain constant region is a heavy chain constant region of human IgG1 and the human light chain constant region is a k chain.

14. The host cell according to claim 7, wherein the host cell is a mammalian cell.

15. The host cell according to claim 14, wherein the mammalian cell is selected from the group consisting of a human, murine, ovine, equine, canine, feline, or a Chinese hamster ovary cell.

16. A method for treating a disorder that would benefit from enhancing the immune response, comprising administering the antibody or the antigen-binding fragment thereof according to claim 1 to a subject in need.

17. The method of claim 16, wherein the disorder is a cancer highly expressing CD47.

18. The method of claim 17, wherein the cancer highly expressing CD47 is a lymphoma.

19. The method of claim 17, wherein the cancer is acute myeloid leukemia or myelodysplastic syndrome.

\* \* \* \* \*